United States Patent [19]
Bro

[11] Patent Number: 5,596,994
[45] Date of Patent: Jan. 28, 1997

[54] AUTOMATED AND INTERACTIVE BEHAVIORAL AND MEDICAL GUIDANCE SYSTEM

[76] Inventor: William L. Bro, 8939 S. Sepulveda #530, Los Angeles, Calif. 90045

[21] Appl. No.: 237,261

[22] Filed: May 2, 1994

Related U.S. Application Data

[63] Continuation of Ser. No. 112,955, Aug. 30, 1993, Pat. No. 5,377,258.
[51] Int. Cl.$^6$ ........................................................ A61B 5/04
[52] U.S. Cl. ........................... 128/732; 128/904; 128/905
[58] Field of Search ............................. 128/731–32, 903, 128/904, 905, 897–98; 364/413.01, 413.02, 41.03

[56] References Cited

U.S. PATENT DOCUMENTS

| | | | |
|---|---|---|---|
| 4,912,552 | 3/1990 | Allison, II et al. | 379/92 |
| 4,933,873 | 6/1990 | Kaufman et al. | 364/413.02 |
| 5,036,462 | 7/1991 | Kaufman et al. | 364/413.01 |
| 5,038,800 | 8/1991 | Oba | 128/904 |
| 5,126,957 | 6/1992 | Kaufman et al. | 364/413.02 |
| 5,142,484 | 8/1992 | Kaufman et al. | 364/413.02 |

Primary Examiner—Angela D. Sykes
Assistant Examiner—John P. Lacyk
Attorney, Agent, or Firm—Cislo & Thomas

[57] ABSTRACT

An automated and interactive positive motivation system (10) that allows a physician, counselor or trainer to produce and send a series of motivational messages and/or questions to a client (50) to change or reinforce a specific behavioral problem. The system (10) consists of a client database (12) and a client program (14) that includes for each client unique motivational messages and/or questions based on the transtheoretical model of change comprising the six stages of behavioral change (100) and the 14 processes of change (114), as interwinding, interacting variables in the modification of health and mental health behaviors of the client (50). The client program (14) utilizes the associated 14 processes of change (114) to move the client (50) through one of the six stages of behavioral change (100) when appropriate by using a plurality of transmission and receiving means. The database and program are operated by a computer (16) that at preselected time periods sends the messages and/or questions to the client (50) through use of a variety of transmission means and furthermore selects a platform of behavioral issues that is to be addressed based on a given behavioral stage (100) at a given time of day.

48 Claims, 8 Drawing Sheets

AUTOMATED AND INTERACTIVE BEHAVIORAL AND MEDICAL GUIDANCE SYSTEM

CROSS-REFERENCED RELATED APPLICATION

This application is a continuation of application Ser. No. 08/112,955 filed Aug. 30, 1993 now U.S. Pat. No. 5,377,258.

TECHNICAL FIELD

The invention pertains to the general field of information exchange services, education and personal health care and more particularly to a computerized telecommunication system that conveys interactive health awareness messages and maintains surveillance over clients by periodically sending behavioral motivation reinforcement messages and/or questions that require a client interaction. The invention further comprises a network service which provides interactive behavioral and motivational guidance to increase healthy behavioral changes in the client based on the client's interaction over a period of time.

BACKGROUND ART

One of the major advances of present-day society is in the field of computerized telecommunications. Today, in the growing field of behavioral medicine, formal verbal interchange is essential to provide modification of behavior and reinforcement. By using computerized telecommunications coupled with voice recognition technology, a client's behavior can be modified and reinforced at the site where behavior occurs and wherever the client goes. It has been found that as the frequency of reinforcing feedback increases, the client shows more rapid progress towards a particular goal. By utilizing a system of continuous computerized reinforcement, a client can be provided with more opportunity and greater frequency of therapeutic contact or feedback than through treatment in person. Additionally, the use of an interactive system vastly increases the therapeutic effect of this method of behavioral modification and reinforcement.

Learning is enhanced through interactive feedback, and feedback in some form heightens the learning experience. The number of times in school a teacher asks any one child for an answer is fairly limited. Most of the time, children raise their hands and respond, and get back a "right" or "wrong." If they are wrong, they have lost their chance, and someone else is called upon for the answer. In traditional adult education and behavioral modification, the amount of continuing feedback is limited to the time actually spent with a counselor or in a seminar. Here, too, the feedback is limited to the actual time the counselor or trainer spends providing interaction with any one client. By contrast, the addition of a computer and telecommunications or broadcast transmission allows "narrowcast" interaction and feedback on a continuous 24-hour basis to the client wherever he goes, allowing for far greater frequency of interaction. Most importantly, in the case of adult behavior modification, this feedback becomes available for the first time at the site where the behavior occurs.

Learning by playing and doing is fundamental to all mammals. While audio broadcast or telecommunications are media based upon hearing, and video broadcast is a medium based upon seeing, interactive feedback utilizing these architectures is a medium based upon doing or responding to the stimulus of feedback. Recent studies have revealed that the single best way to increase mammalian intelligence is through interactive stimulation. The frequency of feedback that we receive generally is the single greatest factor affecting learning and modifying behavior. Further, learning by receiving immediate feedback is preferable to receiving a delayed response. Children prefer interactive television games to merely watching a television program. They become impatient with long strings of dialogue, and the focus of their attention is diverted by devices providing rapid feedback. Adults display the same behavior throughout their lives. For example, when purchasing an appliance, they rarely read the instructions before trying to use it. The need to receive continuing feedback, at all levels of life, is a human characteristic, thus providing a basic survival mechanism which fosters learning and continuing growth.

Research indicates that learning is enhanced by interactive feedback. Where the quantity of interactive feedback is increased, focus is sustained or increased, thereby stimulating keen responsiveness, as is the case with video games. The active involvement required to respond by answering provocative questions stimulates conscious awareness of and focus on the issue at hand. Learning and behavioral modification systems that incorporate rapid feedback foster problem-solving abilities, pattern recognition, management and allocation of resources, logical thinking patterns, memory, quick thinking, and reasoned judgment. Most importantly, when these skills are practiced at the site where the desired behavior is to occur, learning is more vivid and is quickly integrated into real life.

A sense of control is perceived with the provision of feedback. By engaging the client to direct his focus and asking provoking questions, involvement is increased and stimulation results. When the individual learner achieves success and immediately receives positive feedback, self-esteem is rapidly built. When success is rewarded, confidence and resilience are enhanced and knowledge is created.

Historically, individuals have sought self-improvement through self-help books, seminar workshops and programs of aperiodic or short duration. With the best of intentions relapse usually occurs within several days after reading a book or attending a seminar, or several months after the conclusion of a behavioral modification program.

In contrast, computer-derived, self-adjusting motivational guidance, which interactively polls the client and comments on his performance as he goes about his daily life throughout the year, has a more lasting effect. It differs importantly from seminars and visits to counselors in that it modifies behavior at the site where the behavior occurs, with personal or customized intervention. The more frequent interactive dialogue between the counselor-controlled computer and the client enhances the feedback and therapeutic simulation in much the same way as has been experienced in other interactive communication structures, such as education and entertainment. For instance, consumers accord a higher value to interactive entertainment software than to passive software, due to the greater stimulation afforded by this mode. In entertainment software, an example would be some of the new video games that present a mode which runs like an animated cartoon until one elects to interact. As an animated cartoon, the video usually becomes boring within minutes. But as an interactive video game, the software stimulates the user with hours of entertainment.

Furthermore, interactive text based online services now enable people using personal computers or other access devices to interact with other people using telephone line connections channeled through a central host computer. Since the early 1980's, the range of services and the number of people using online services have grown significantly. In addition, increased exposure to computers in the workplace and at school has resulted in growing use of computers in the home.

Also, technology advances have reduced the size of personal computers and have led to an increasing range of mobile personal computers, including laptops, notebooks and pocket computers and other electronic devices such as the Personal Digital Assistants (PDA's) and Personal Communicators. Increasingly, these devices incorporate telecommunication capabilities which enable them to access online services at work, at home or while traveling.

The effectiveness of both the telephone and the computer and online services has been shown to dramatically affect behavior due to their potential to give an increased dose of reinforcement on a continuing basis in the environment where the behavior occurs. As software and hardware platforms advance in sophistication, the opportunity will grow dramatically to further create realistic and engaging motivational support and guidance.

Therefore a need exists for a computer-driven interactive two-way communication link that increases the opportunity to create realistic and engaging behavioral reinforcement and guidance in the home or office and at remote locations with both stationary and portable wired and wireless communication devices.

Furthermore, psychotherapy outcome studies have been aimed at understanding how people change their behavior with and without the use of psychotherapy counseling. The results of these outcome studies have produced a definitive structure or model of the process of change that underlies both self-initiated and therapy-assisted modification of human behavior.

More particularly, the structure or process of behavioral change has been defined into six separate and distinct stages which have been observed by researchers. These distinct stages are variously known as precontemplation, contemplation, preparation, action, maintenance and relapse. Relapse can occur at anytime. It represents the failure of the individual to sustain the new behavior.

In surveying the individual or core fundamental therapeutic techniques utilized variously in 300 to 400 forms of counseling and self initiated help by individuals, researchers have derived 14 fundamental processes for moving a person from one behavioral stage to another. These individual processes are now seen to be operant mechanisms for personal growth and transformation. In the past almost all intervention programs for both physical health and mental health behavior problems have been based upon individual theories posited about how individuals proceed through therapeutic transformation. Now, with the recent abstraction and derivation of these 14 fundamental processes, it is possible to direct the construction of the content of therapeutic interventions according to a successfully derived model or format. While the greatest amount of research in this area of refining and applying these 14 processes has been initially in the field of smoking cessation, subsequent research has indicated the universal applicability of these processes across a wide range of human learning and behavior.

In the past, these individual processes have been administered ad hoc or randomly by various counselors in verbal change processes in person or through various methods including but not limited to bibliotherapy, (reading motivational literature) direct telephone counseling, group therapy classes and seminars. Furthermore, it must be remembered that outpatients on the average spend about 99% of their waking weeks outside of the therapy situation. There are advantages to having therapy and behavioral guidance parallel self-change efforts that clients make outside of therapy into their daily lives. The disadvantages of the prior art are overcome by the present invention which provides a more comprehensive approach while affording greater convenience and increased interactive contract for physicians, psychotherapists and various counselors.

Therefore, a need exists to apply and distribute these 14 processes individually and collectively through the medium of computerized telecommunication. More particularly, this need is magnified due to the large number of variables and combinations in timing the administration of the 14 processes within the 6 stages of the change process on an individualized basis. The computerized administration and transmission of these individual processes both separately and collectively is a novel and unique advancement not known in the art.

In summary, a computerized interactive system increases the client's ability to resolve problems at the site where behavior occurs, and adjusts him within the framework of a preset goal. By including, within the context of the personalized message, challenges in the form of questions, an entertaining and stimulating process can be added due to the increased feedback or interactive nature of new telecommunication technology.

With regard to the prior art, many types of systems have endeavored to provide an effective means for providing surveillance over the behavioral modification of a patient or client by using a telecommunication link. However, these prior art systems have not disclosed an adequate and cost-effective telecommunication network that uses a computer in combination with a telephone or other platforms to provide positive motivational messages and/or questions that are answered by a client by means of a dual tone multifrequency telephone set or other platforms.

Further, the prior art systems have not disclosed utilization with such hardware as voice stress analyzers, on line services, olfactory units, CD-ROM platforms, interactive television in connection with a telecommunication link as a further behavioral modification means in use with the client.

A search of the prior art discloses patents that show different types of feedback mechanisms:

| PATENT NO. | INVENTOR | ISSUED |
| --- | --- | --- |
| 3,742,938 | T. J. Stern | 03 July 1973 |
| 3,808,694 | W. Y. Hutchinson et al. | 07 May 1974 |
| 4,112,425 | G. J. Zobrist et al. | 05 Sep. 1978 |
| 4,237,344 | J. R. Moore | 02 Dec. 1980 |
| 4,328,494 | R. Goodall | 04 May 1982 |
| 4,377,214 | G. G. Hansen et al. | 22 Mar. 1983 |
| 4,396,976 | G. P. Hyatt | 02 Aug. 1983 |
| 4,602,127 | J. F. Neely et al. | 22 July 1986 |
| 4,773,492 | E. Ruzumna | 27 Sep. 1988 |
| 4,831,242 | W. H. Englehardt et al. | 16 May 1989 |
| 4,835,372 | Gombrich et al. | 30 May 1989 |
| 4,916,435 | K. L. Fuller | 10 Apr. 1990 |
| 4,922,514 | Bergeron et al. | 01 May 1990 |
| 4,912,552 | Allison III et al. | 27 Mar. 1990 |
| 4,933,873 | S. B. Kaufman et al. | 12 June 1990 |
| 4,952,928 | G. T. Carroll et al. | 28 Aug. 1990 |
| 5,008,835 | E. F. Jachmann et al. | 16 Apr. 1991 |
| 5,014,298 | R. A. Katz | 07 May 1991 |
| 5,018,736 | T. R. Pearson et al. | 28 May 1991 |
| 5,023,901 | P. Sloan et al. | 11 June 1991 |
| 5,036,462 | S. B. Kaufman et al. | 30 July 1991 |
| 5,038,800 | K. Oba | 13 Aug. 1991 |

-continued

| PATENT NO. | INVENTOR | ISSUED |
|---|---|---|
| 5,068,080 | A. J. Impink Jr. et al. | 26 Nov. 1991 |
| 5,085,527 | P. A. Gilbert | 04 Feb. 1992 |
| 5,126,957 | S. B. Kaufman, et al. | 30 June 1992 |
| 5,127,003 | W. J. Doll, Jr. et al. | 30 June 1992 |
| 5,142,484 | S. B. Kaufman, et al. | 25 Aug. 1992 |
| 5,170,426 | F. D. D'Alessio, et al. | 08 Dec. 1992 |
| 5,189,395 | M. S. Mitchell | 23 Feb. 1993 |
| 5,206,897 | N. Goudreau, et al. | 27 Apr. 1993 |
| 5,218,344 | J. G. Ricketts | 08 June 1993 |
| 5,219,322 | L. R. Weathers | 15 June 1993 |
| 5,224,173 | R. J. Kuhns, et al. | 29 June 1993 |
| 5,245,656 | S. K. Loeb, et al. | 14 Sep. 1993 |

The Sloan et al., patent discloses a surveillance system which integrates voice identification with passive monitoring mechanisms. The system comprises a central station located at a supervisory authority and a plurality of remote voice verification units. Each unit is located at a designated locality for an individual under surveillance and is connected to the central station via telephone lines. The central station consists of a control computer system and a violation computer system. The central station maintains and analyzes all relevant data for each individual, and initializes and retrieves information from each voice verification unit. Each voice verification unit conducts a voice verification test of a respective individual according to test schedules outlined by the central station. Test and monitoring results obtained during a defined surveillance period are transmitted to the central station on a periodic or exigent basis. Each remote station has a modem input, test means input connected to a microphone, and a third input to receive passive monitoring signals. The active and passive signals are analyzed according to an algorithm and command signals received from the central station. The test means also has an output to prod the individual to speak a preselected series of words. The test schedule in each remote is randomly created for each period and individual.

The Fuller patent discloses a remote confinement monitoring station and system with a central office that provides means for automatic selection of a specific confinee. The central office selects scheduled or semi-random monitoring calls, to avoid a high degree of predictability by the confinee, auto dialing means for transmission of a prerecorded or synthesized audio instruction message to the confinee, and recording of information received in response to the acts of the selected confinee preformed in response to the communicated message. The central office has a computer with a telephone line modem, a voice synthesizer, and other accessories in displays for automatic recording of data received including a visual camera image and breath analyzer results, and can include automatic image comparison and violation signal alarming.

The Moore patent discloses a rapid response hospital health care communications system. The system includes an auto dialer telephone system to allow patients to communicate from outside the hospital to receive advice and health care as indicated by the patient's medical profile. The communications system includes a health care console with an information storing computer connected through various communication paths to in-hospital patients, and by telephone means to out-of-hospital patient locations. Each out-of-hospital location includes a communication interface with a telephone, a console, and a hand-held remote control comprising a plurality of sensors, indicators and features. The interface includes an auto dialer and auto identifier that dials the health care console and identifies the patient by a computer recognizable code.

The Kaufman et al., patent discloses an interactive patient assisting device that has both preselected doses of medicine and a physical testing device that can communicate with a remote medical center over the telephone system. The system includes a clock/calendar unit that can be programmed to establish a schedule of a variety of activities, a pharmaceutical dispenser, a voice synthesizer and recognitions unit, a computer, displays, and monitor means for blood pressure, oxygen and temperature. For communicating to a remote location, an automatic dialer, modem and telephone are included.

The Bergeron et al., patent discloses a method and system for the dispatch of resources to remote sites in response to alarm signals. A processor accesses the database of, for instance, a field service engineer designated to provide services to particular remote sites in response to the alarm signals received from those sites. The processor then attempts to establish a telephone connection with the field service engineer and provide the engineer with information by means of synthesized voice messages. The system may execute remote diagnostic programs and determine the results and attempt to communicate with selected resources. The system has a conventional processor with a database, voice synthesizer, voice system and auto dialer. When the system dials and the telephone is answered, the system requests an identification code by means of the touchtone buttons before it communicates.

The Hutchinson patent discloses a weighing and height measuring device. It is especially adapted for use with a remote digital read-out system. The device comprises a weight responsive moving platform connected by cable to a remote digital read-out unit. One of the objects of the invention is to provide a weight measuring device adapted for use with a remote read-out and/or computer input device.

The Stern patent discloses a cardiac pacer and heart pulse monitor for remote diagnosis wherein information from a pair of sensors is transmitted by means of a telephone handset and transmitter, over a commercial telephone system to a remote receiver. Information received at the receiver may then be processed by means of an appropriate computer and program system.

The Carroll patent discloses an adaptable electronic monitoring system. The system is configured to fit the needs of a particular monitoring or identification application by selecting appropriate modules. The system provides for monitoring at a central location and communication between the location of the sensed information to the processing site by means of a normal telephone communications system.

The Doll patent discloses a digital/audio interactive communications network. The digital network may be a wide area, metropolitan or local area network, and may communicate with other networks. The digital network ties a digital LAN server and an audio server together. The system works with software directed to a client/server architecture in an application that requires recording and playback of audio information.

The D'Alessio patent discloses a method and system for home incarceration using a telephone network and voice verification. The system has a control center with a process server connected to controllers through a LAN such as an ethernet or wide area network. New inmates are added by voice training so that the system can create voice templates of selected words. A data base of the voice templates and phone numbers, work schedules, etc. is created. Calls received are screened by using caller ID. Calls to and from the inmate are performed on a predetermined or random frequency, the frequency being a function of the patient's behavior. All activities are maintained in a log file.

The Ricketts patent discloses a method and system for monitoring personnel using computers and transceivers and a network. The interactive system monitors the identity and location of the inmates of a correctional facility, hospital, school or the like, and can alert the inmate that the inmate is entering a restricted area, or being approached by another inmate within a predetermined threshold distance. The inmate's transceiver can include a bar code for use of vending machines, telephone and the like, with the transactions being allowed or denied by the computer.

The Weathers patent discloses a psychotherapy apparatus and method for treating undesirable emotional arousal of a patient. The system presents visual and audio stimuli in each ear and eye separately and synchronously and alternately, the presentation being controlled in response to the patient's physiological responses to the stimuli. In addition to the behavior modification stimuli supplied to the patient by the computer, an operator, using a microphone, can direct the patient's attention.

The other cited patents are for background purposes and are indicative of the art to which the invention relates.

It will be noted that the above mechanisms and systems do not allow the utilization of various well known elements used in a unique random calling manner with a client database and client program of prescribed messages and/or questions for particular persons. More particularly, the instant apparatus and method provides a uniquely reinforcing approach of allowing the use of prescribed messages and/or questions for particular persons. More particularly, the instant apparatus and method provides a uniquely reinforcing approach of allowing the use of random calls at random locations from a list of possible locations where a client may be located. Furthermore, this system utilizes existing telecommunication technology including pagers, online services, etc., unlike many of the devices described in the above referenced patents.

SUMMARY OF THE INVENTION

The automated and interactive positive motivational system is designed to be used by doctors, psychologists, counselors or other trainers to provide motivational messages and/or questions to clients having behavioral and various addiction, volitional or motivation problems. Its basic configuration comprises:

(a) means for recording and accessing a client's database that includes for each client the name, schedule of telephone numbers where the client may be reached during each 24-hour period, personal identification number, and previous history of messages and the client's responses;

(b) means for measuring and recording a client's weight without revealing their weight to them and transmitting said weight information telephonically for use in a weight reduction program;

(c) first means for recording and accessing a client's program that includes for each client specific motivational messages, personal and unique metaphoric references, and/or questions that are to be responded to by the client through either the telephone, one- or two-way interactive beeper, personal communicator, modem, personal computer, or interactive television;

(d) a computer having means for accessing the client database and said client program. If a match is found between a client's database and client program, the computer produces a sequence, a digital telephone signal and corresponds to a client's telephone number or beeper or personal communicator number, a digital client validation request signal and a digital motivational message(s) and/or questions. The messages and/or questions are only then sent if the client's validation request signal is responded to by the client with a valid personal identification number (PIN) in the telephone mode, or broadcast without a PIN with or personal communicator;

(e) means for converting the digital signals produced by the computer to telephone tone signals that are sent to a client's dual tone multifrequency telephone set or computer and modem via a telephone network. The telephone set is used to respond to the computer's validation request, hear the motivational message(s) and/or to respond to the questions;

(f) means for converting the telephone tone signals originating at the client's telephone set, personal computer, or hand-held wireless device, to digital signals for application to and processing by the host computer; and (g) second means for permanently recording all the outgoing and incoming client communications.

An important object of the invention is that the system manipulates speech messages that are stored, not in an analog format common to audio tape storage systems, but in digital format that is stored on a read-only compact disc, a computer hard drive or the like. The use of compact discs allows the system to access files quickly and accurately. Therefore, it is possible for the computer to access more than one speech file at a time. Each telephone line that the system is servicing is actually a small "slice" of computer time during which speech files are being played from or recorded. The more lines that are active, the more slices of time that must be managed. The system provides the functions to operate with more than one telephone line simultaneously, thereby allowing a physician or other counselor, at all times over a 24-hour period, to process and supervise many more clients than otherwise. In addition, the system allows for a client to receive more doses of intervention over any time period than in any other manner.

Another object of the invention is directed to accomplishing most tasks in a voice response application by accepting, recognizing and making decisions based on a keypad input from the caller's dual tone multifrequency telephone. The keypad generally sends dual tone multifrequency (DTMF) tone signals but occasionally multifrequency (MF) tones are used by certain types of telephone switching equipment. While these two signalling methods are not compatible, the system will work with either one equally well.

Still another object of the invention is the use of digitized voice signals for the transmission of messages to the client. Digitized voice signals are typically made by sampling the voice wave form 6000 to 8000 times per second in order to accurately reconstruct good speech quality. Each sample takes 8 to 12 bits, this results in 48,000 to 96,000 bits of information per second that must be stored. It is common in telephonic applications for a digitized voice to be compressed by storing only the differences between samples. Therefore, the speech card that the system supports uses a compression technique known as Adaptive Differential Pulse Code Modulation (ADPCM) which recognizes that there is only a small difference between the speech samples and stores a logarithmic function of the difference between speech samples. The result is good speech quality at only 3000 bytes per second of data throughput.

Yet, another object of the invention is that the client program may be directed to any subject matter such as motivational training, teaching, psychological behavior modification, religious training, indoctrination and reinforcement by sales managers, psychologists, ministers, counselors, wherever motivations would be facilitated by daily or periodic intervention. The following is a partial list of some of the component areas that the client program may be directed to:

1. nutrition
2. creativity
3. exercise
4. weight loss (diet/weight management)
5. optimism (and hope)
6. life-long learning
7. time management
8. stress management
9. happiness (and purpose)
10. optimal health management
11. relationships
12. thrift/financial freedom (reduction of consumption)
13. risk/courage
14. new, balanced image, enhanced self-image (beauty)
15. immune system enhancement
16. midlife transformation/emergence
17. women and men in aging and transition (heart disease, menopause, etc.)
18. control or self-discipline
19. intuition enhancement
20. high energy
21. spiritual insight
22. compliance with medical requirements
23. pain control
24. anger management
25. acceptance of mortality
26. reforming the concept of aging
27. goal management
28. memory management
29. reformation of self-destructive behavior
30. transformation of regret
31. anxiety management
32. mental and physical resilience
33. early cancer screening and detection
34. an interactive journal
35. wake up and sleep meditations
36. control of performance anxiety and mental rehearsal
37. guided imagery
38. enhanced self-esteem Accordingly it is an object of the present invention to record the daily or periodic activity schedule of each client enabling contact with the client on a scheduled or random basis by telephone, personal computer or other means such as a wireless alpha-numeric pager, laptop computer, personal communicator, cellular phone, or modem that is used to contact clients wherever the client may be during the day or night. If the client misses a call, they may call in to the computer and get their message by using a specific password.

Yet a further object of the invention is that the client program may be directed to utilizing the recently discovered transtheoretical model of change comprising the six stages of behavioral change and the 14 processes of change, as interwinding and interacting variables in the modification of health and mental health behaviors of the client. These six invariant stages of behavioral change, which have been identified and to which the client program may be directed, are:

1. Precontemplation
2. Contemplation
3. Preparation
4. Action
5. Maintenance
6. Relapse The client program further includes the associated 14 processes of change utilized to move the client through the six stages of behavioral change. The following is a list of these 14 process areas that the client program may be directed to:

A. Consciousness raising
B. Self Liberation
C. Social Liberation
D. Self re-evaluation
E. Environmental re-evaluation
F. Counter conditioning
G. Stimulus control
H. Reinforcement management
I. Dramatic relief
J. Helping relationships
K. Self efficacy
L. Temptations to relapse
M. Decisional pros
N. Decisional cons The object of the present invention is to utilize these 14 processes within the previously cited six behavioral stages of individual growth through computerized management and administration by initiating prompts and cues and related educational material for guidance and reinforcements by the client program.

Another object of the invention is that the client program may be directed to the field of chronic disease detection. More particularly, the client program will provide periodic behavioral cues to aid in the early diagnosis and cure of such chronic diseases as glaucoma, dental and periodontal disease, cancer, heart disease, and diabetes. In addition, the client program can address issues for the management of such chronic diseases as diabetes and hypertension where compliance with medical regimen can be critical. By applying the aforementioned transtheoretical model, the client program will provide the gradual courage to overcome individual resistance and to reinforce periodic self and physician examinations.

Yet another object of the present invention shall be the formulation and publication of individually customized information in the form of reports, or graphs, indicating performance and response profiles, educational monographs, and tutorials and other materials necessary for providing motivation and education. By storing in a data base memory device a group of prerecorded informational data of a generalized nature and accumulating personal response profiles in said memory device, it is possible to mix or formulate a customized, unique and individual printed educational document.

Therefore, another object of the present invention would be that for each individual client, based upon his education, gender, age, demographic profile, psychological profile and prior response profiles, an educational document and text would be formulated according to the individual's present behavioral stage.

A further object of the present invention is to provide a large central mainframe computer or interconnected series of P.C.'s containing thousands of microprocessors which could be used by local or regional clinics and hospitals for interactive, telecommunication and/or multivideo transmission for enabling thousands of individual clients to be provided interactive medical guidance and feedback in real time or delayed service, whereby a hospital may currently serve a greater outpatient population in its locality and place increasing emphasis on home health care.

Another object of the present invention is to use the asynchronous transfer mode (ATM) as an alternative method of transmission for behavioral guidance and motivational reinforcement. Since the present invention relies upon telecommunications which are transmitted or delivered synchronously, this alternative embodiment relates to the asynchronous transmission of information by both wire and wireless means in private and public networks. Therefore, an additional object of the present invention is to use the asynchronous transfer mode for both data and real time and delayed transmissions; as an example, voice and video wherein it is equally adaptable to both local and wide area networks.

The rationale of the system is that man is in a continuous state of growth and development. The system provides the motivation through continuous daily monitoring of each client as he works towards their basic goals for optimal health, personal success, longevity and happiness. By this daily or periodic reinforcement and guidance utilizing interactive feedback, the system is able to maintain the organization and intervention between the client and his goals.

By mobilizing patients to accept responsibility for their own health through behavioral guidance in preventive health programs and to comply with medical prescriptions in the dispensing and taking of medicines, large savings can thereby be realized, contributing to national goals of medical cost containment. The aging of the population necessitates greater health care expenditures which in turn are aggravated by the possibility of older individuals having one or more chronic diseases wherein noncompliance with medical regimens can become financially costly, dangerous and even life-threatening.

These and other objects and advantages of the present invention will become apparent from the subsequent detailed description of the preferred embodiment and the appended claims taken in conjunction with the accompanying drawings.

DESCRIPTION OF THE PREFERRED EMBODIMENT

Figure 1:
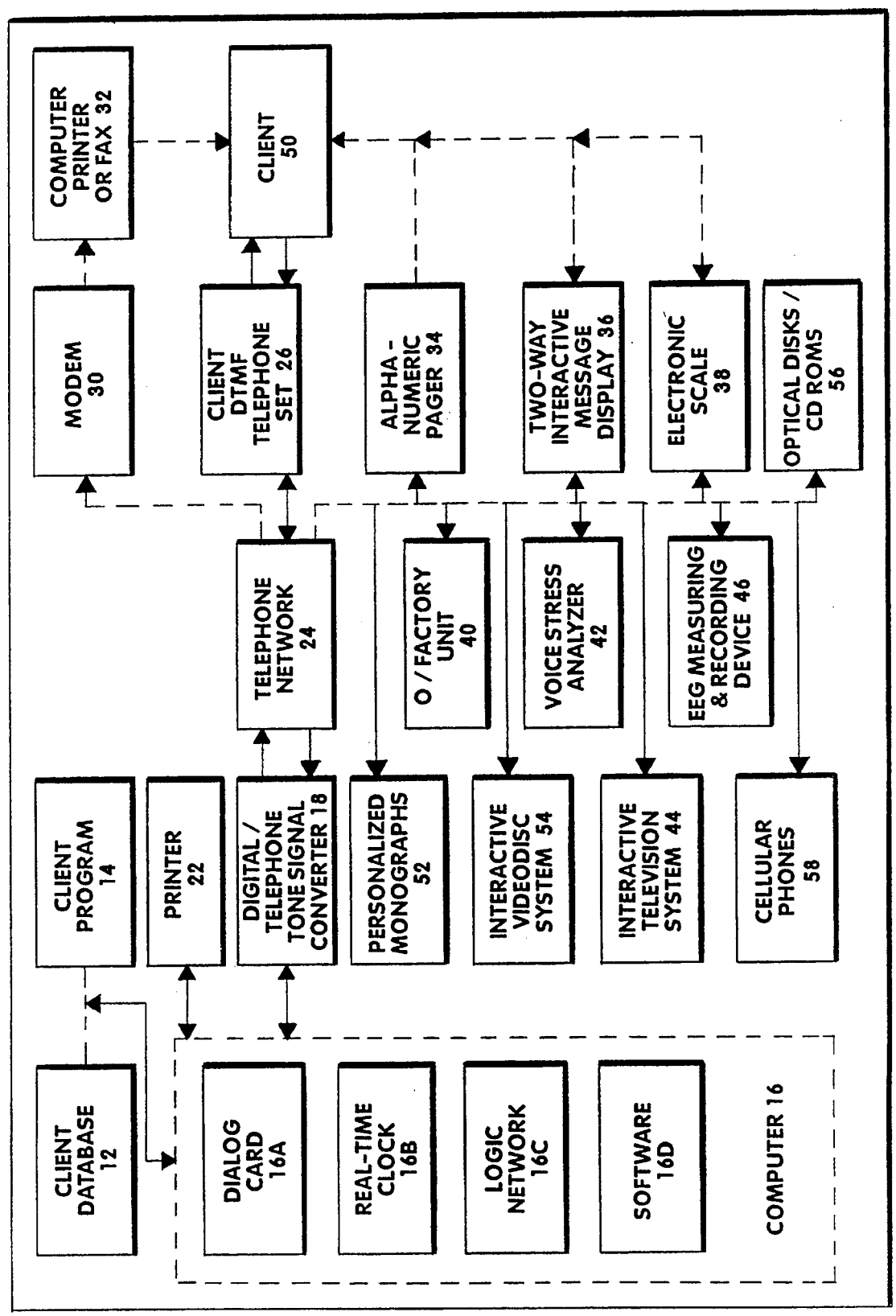
FIG. 1 is a block diagram showing the interactive activity between the system and a client.

The best mode for carrying out the invention is presented in terms of a preferred embodiment that is designed to allow doctors, psychologists, counselors and other trainers to maintain surveillance over their clients by utilizing a wired or wireless telecommunication link to perform automated information exchange. The preferred embodiment of the automated and interactive positive motivation system 10, as shown in FIG. 1, comprises a means for recording and accessing a client's database 12 and a client's program 14, by using a computer 16, having a digital signal/telephone tone converter 18 and a printer 22, wherein access means comprise a telephone or other wired or wireless telecommunications network 24 and a client dual tone multifrequency telephone set 26. A client 50 uses the system 10 which can also be enhanced by the incorporation of the following elements that are operated by the aforesaid network 26: a modem 30 that operates a computer printer of facsimile machine 32, an alpha-numeric one-way or two-way pager 34, a two-way interactive message device 36, an electronics scale 38, an olfactory unit 40, a voice stress analyzer 42, an interactive television system or personal computer 44, an EEG or blood sugar or blood pressure or heart monitor or cholesterol measuring and recording device 46, personalized monographs, Level III interactive video, optical discs, i.e., CD-ROMs, cellular phones, and a timing device 47 for measuring response latency.

The client database 12 in the preferred embodiment consists of a compact disc (CD) recording that is played back on a CD player that interfaces with the computer 16 as shown in FIG. 1. However, other database recording and playback units can also be used. By way of example but not of limitation, these units include but are not limited to hard disks or other random access memory devices or a tape cartridge that is played back to the computer by means of a tape cartridge player or an optical disc and optical disc playback unit. The client database includes for each client 50, the client's name, their calling schedule by week, day and time, each client's personal identification number (PIN), and previous history of messages received and response profiles.

The client program 14 in the preferred embodiment, is also recorded and played back by a CD player or other recording and playback units, as described above for the client database 12, and is connected to the computer 16 and to the telecommunications network 24 as shown in FIG. 1. The client program 14 is especially designed to serve a plurality of specific clients. The program 14 can include as many motivational and reinforcement messages as are necessary to help with a specific behavioral problem. The motivational and reinforcement messages are designed to provide therapeutic intervention at specific or random times and more particularly to provide therapeutic intervention at the site and appropriate time where the behavior to be corrected occurs. In the field of behavioral reinforcement it has been found that even with the best of intentions, relapses usually occur within several days following the reading of a book or attending a seminar to several months after the conclusion of a behavioral modification program. Thus, by transmitting behavioral motivation and reinforcement messages on a periodic or random basis, the behavioral modification program can continue on course to a curable conclusion.

In addition to or in combination with the messages, the system is also designed to send a client behavioral modification polling questions. These questions may be answered by the client by pressing on a specific key on the keypad of the dual tone multifrequency telephone set 26 or by use of a speech recognition device. The answers to the questions are analyzed by the client's doctor or trainer to find root problems and to determine the next series of messages and/or questions that are to be transmitted to the client 50 at the next transmittal period. All messages, questions and the client's response to the questions as well as the time, date, duration of each call and touch tones entered by the client 50 are retained in a permanent log or record by means of the printer or other type of storage device 22 which is directly connected to the computer 16 as shown in FIG. 1.

The telephone by its very nature, has always been interactive on a two-way basis and because of its wide usage it lies within the comfort zone of nearly all clients. The telephone is also cost effective and is convenient for both the caller and the client. Additionally, social learning theories suggest that education carried out in the setting in which the behavior is taking place will have the greatest impact. Thus, telephone counseling at home or in the work place may have greater behavioral impact and relevance than that within the clinic. For clients who cannot come to a clinic because of their physical condition, distance or the presence of a psychiatric disorder that makes the intimacy of face-to-face contact intolerable, the telephone or other remote communications device is the sole available means for counseling. By calling clients on their transportable cellular telephones or other portable communication devices 58, behavioral reinforcement can also be provided for busy clients on the go and increase the instances wherein motivation can be provided in the place where the behavior occurs.

The client database 12 and client program 14 interface with the computer 16 that in the preferred embodiment consists of a personal computer. The client database 12 and client program 14 as described above, are externally stored as shown in FIG. 1. However, these elements may also be stored on a hard disc located within the computer 16 or on other mass media storage devices such as CD-ROM or removable mass media cartridges. The computer 16 is configured in part to include a speech card such as a Dialogic D41 4-line or larger 16A, having a real-time clock 16B and a logic network 16C, operated by the system software 16D.

The Dialogic type card or other similar device 16A allows a speech compression technique to be used that samples a small difference between speech samples and stores a logarithmic function of the difference between the speech samples. This technique results in good speech quality at only 3000 bytes per second. The real-time clock 16B sets and selects the appropriate time for a particular client to be accessed from the client database 12 and the client program 14. The logic network 16C provides the logic necessary to determine if a match between the client stored in the database 12 and in the client program 14 is available. The system software 16D provides the algorithms to operate the system 10 in combination with the logic network 16C. The operating steps of the software program are shown in the software flowchart included as FIGS. 2A and 2B.

Figure 2A:
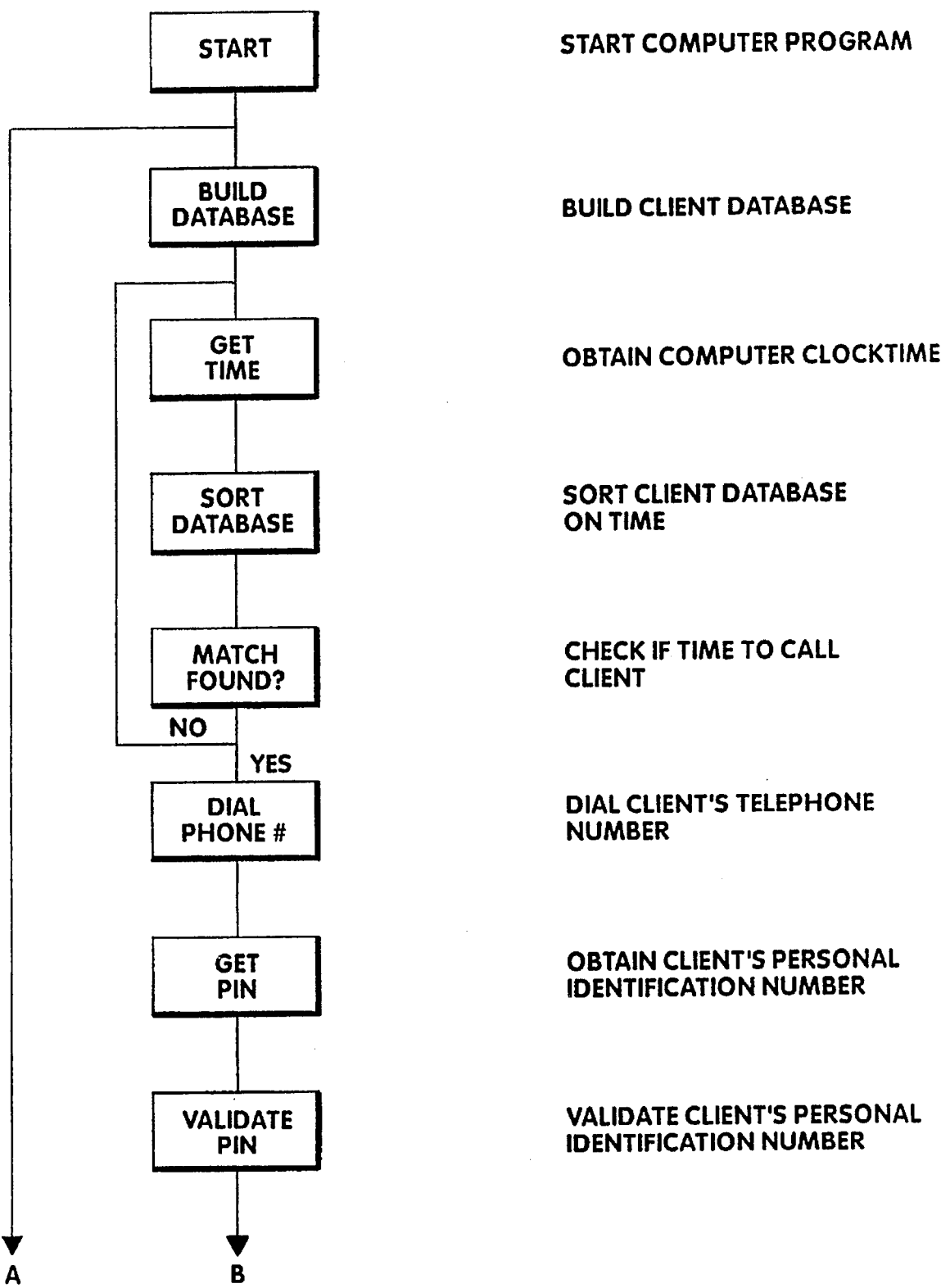
FIG. 2A is an application flowchart of the computer software program.
Figure 2B:
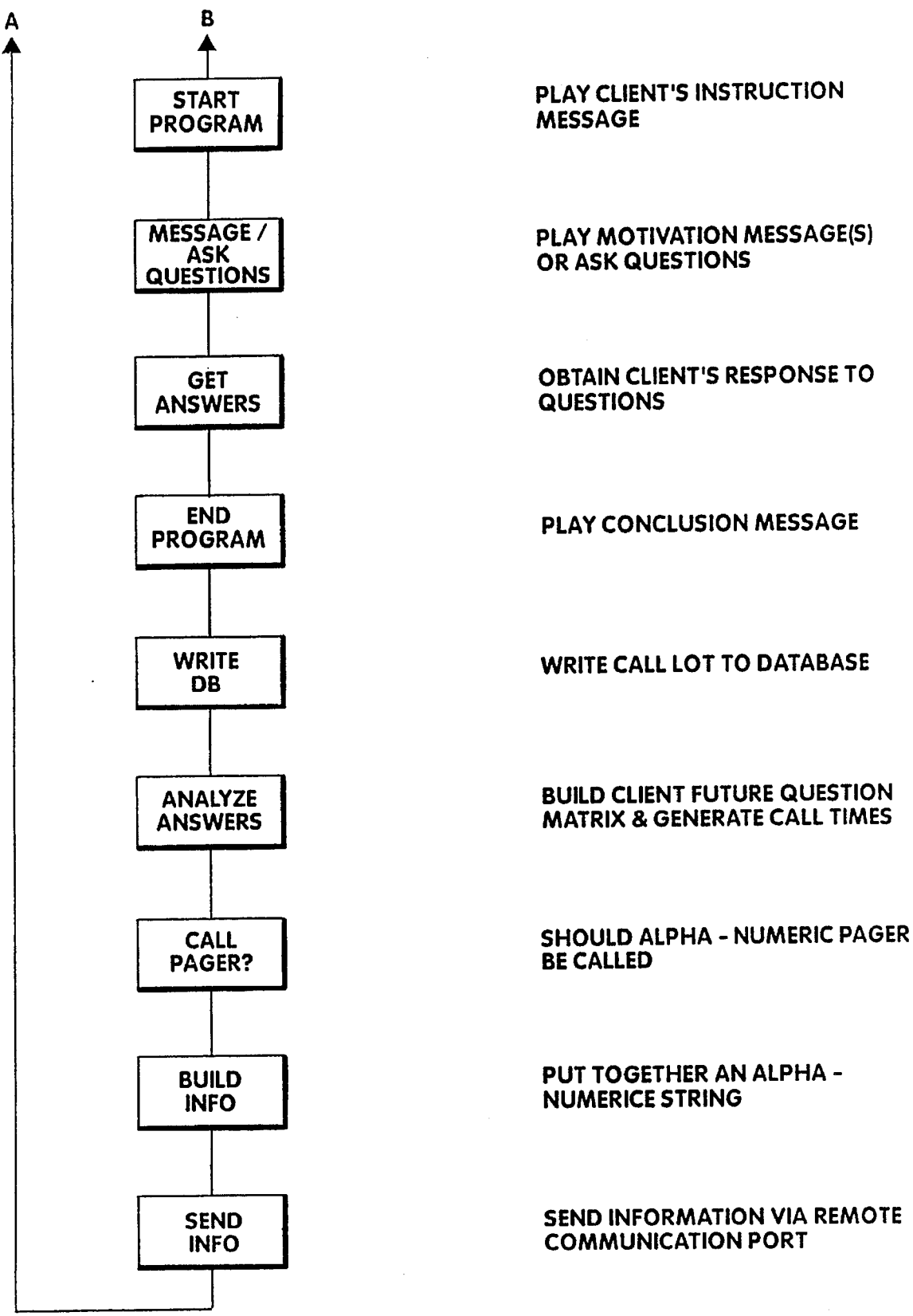
FIG. 2B is a continuation of the application flowchart of FIG. 2A.

As shown in FIGS. 2A and 2B, the computer program builds a client database and sets the database to a computer clock time. In a typical operating sequence, the computer 16 at a preselected week and time, accesses the client database 12 and the client program 14. If a match is found between the client's database 12 and program 14, the computer 16 via the logic network 16C, produces in sequence, a digital telephone number and a digital client validation request signal.

Both of these signals are applied to the digital signal/ telephone tone signal converter 18. The converter 18 includes circuit means to accept and convert the digital signals from the computer 16 to telephone tone signals that correspond to the client's telephone number and a personal identification number. The converter 18 can also be designed to include a telephone number redial circuit and a random telephone number dialer circuit. The redial circuit allows a client's busy telephone number to be automatically re-dialed at selectable time intervals. The random number dialer allows client telephone numbers stored in the client database 12 to be randomly selected and called.

From the digital signal/telephone tone signal converter 18, the telephone tone signals are applied as shown in FIG. 1 to a telephone network 24. The network 24 relays the tone signals to the client's dual tone multifrequency telephone set 26 from where the client 50 can answer the telephone 26 and respond to the request to provide a personal identification number. The client 50 responds by pressing on specific keys on the keypad of the telephone set 26. If the client 50 responds with a valid number it is routed via the telephone network 24, back through the converter 18 to the logic network 16C in the computer 16. Upon the receipt of a valid number, the logic network 16C enables the client program 14 to allow the audio signals carrying the messages and/or questions to be transmitted via the telephone network 24 to the client's telephone 26 from where the client 50 can receive the message and respond to the questions.

The telephone network 24 used in the preferred embodiment is serviced by the local telephone public utility company. However, if a closed circuit operation is desired, such as within the confines of an enclosed area or building, a private telephone network or Local Area Network (LAN)

may be employed. In either of the above scenarios the clients dual tone multifrequency telephone set 26 may be hardwired to the telephone network 24 or, a transportable cellular 58 or a two-way pager 34 that uses RF or satellite communication links may be used. By calling a client 50 on their transportable cellular telephone or other device 58, the motivation message can in many instances be sent to the place when the behavior is occurring when the message carries its greatest effect. As also shown in FIG. 1 by dotted lines, in lieu of making the initial client contact by using the telephone set 26, the contact can be made by means of a modem 30, an alpha-numeric pager 34, a two-way, interactive, computer activated message display 37 or other such devices. If a modem 30 is used, it can be connected directly to a computer printer or facsimile machine (FAX), text screen telephone or on-line system 32. In this client alerting medium, after the client 50 receives a motivational message or a question, the client 50 response can be made by calling the computer 16 on the dual tone multifrequency telephone 26 by use of a special computer access telephone number. Likewise, if an alpha-numeric pager 34 is used the client response would be made as previously described.

The use of a two-way interactive message display 36 further provides an enhanced client interface in that text and graphics can be included with the messages and questions. The display 36 is connected directly to the computer 16 via the telephone network 24 and digital/telephone tone signal converter 18. Additionally, screen and textual media position the software developed hereunder for future interactive television and multimedia applications when they commercially appear and may be added to the system.

Although not shown, it may be envisioned in one embodiment that a one-way or two-way, interactive message display 36 be in the form and design of a ladies' compact containing a mirror. The compact 36 comprises a small screen for the reception of alpha/numeric data which it receives over existing paging networks, and in addition, as an option, it may receive wireless voice transmission over a built-in speaker. For transmission purposes, the compact 36 comprises four (4) response buttons which allow the client 50 to respond to the messages and questions received either as data on the alpha/numeric screen or as audio transmission from the built-in speaker. In use, the compact 36 would utilize the before described cellular wireless PCS or PCS modes and would operate on either analog or digital transmission.

Another embodiment would be a wrist communicator which would be used for providing behavioral modification through a one-way or two-way interactive message display 36 and designed to be attached to the wrist with a flexible band. The aforesaid device would receive data from paging networks or via wireless voice transmission and display the data on an alpha-numeric screen. For transmission purposes, the wrist unit 36 would contain response buttons, allowing the client 50 to respond to messages and polling questions transmitted from the personal communication device or via cellular transmission. Both the aforesaid ladies' compact 36 and the wrist unit 36 could operate through a variety of transmission modes in either analog or digital format.

Additionally, a unique software program which is commercially available instructs the computer to send text messages which are encoded to activate special software algorithms contained within the computer 16 receiving the messages via the modem 30. This special software contained in the receiving computer will activate either internal or external speakers or telephone handset in order that the text messages may be heard as the text scrolls across the screen. The aural sound emphasizes and enhances the text presentation, or the client 50 may choose to listen and not read the text while performing other tasks.

Likewise, an interactive television system 44 can be used wherein customized broadcasts can be responded to by individual clients or whole classes of subscribers, providing a low cost alternative to individual customized instruction. In addition to or in lieu of an interactive television system 44, an interactive videodisc system 54 comprising a videodisc player or similar means such as a CD-ROM or the like and monitor interfaced with a microcomputer may be used.

Additionally, the aforementioned speaking screen embodiment is equally applicable to all screen media, such as the aforementioned interactive television, screen telephones, personal digital assistants, communicators and computer terminals.

Alternatively, the aforementioned interactive data communications may be performed by asynchronous transfer mode or other suitable protocols instead of the currently available synchronous transfer mode commonly used to transmit digitized voice. The asynchronous transfer mode is one of a general class of digital packet switching technologies that relay and route traffic by means of an address contained within a very short, fixed-length packet referred to in the industry as a cell. Therefore, it is envisioned that the system 10 may utilize a packet switching technology as the aforementioned asynchronous transfer mode to route traffic by means of addresses contained within packets, in contrast to the synchronous transfer mode or STM technologies that route data over dedicated physical paths that are established during call set-up and remain fixed for the duration of a call. With the system 10 using asynchronous transfer mode, the creation of local area networks or LANs can be used for the mounting volume of traffic generated by the current client behavioral program. Moreover, unlike other transfer modes, an asynchronous transfer mode provides two further benefits: (1) it positions local area networks for future multimedia applications if they appear when more clients are added to the system, and (2) it seamlessly integrates local traffic into the future wide area asynchronous transfer mode network.

With the use of optical discs or CD-ROMs 56, CDI and similar devices a computer-based information metering system is envisioned wherein a client 50 may be billed through the use of an encryption-metering device only for amount of therapy the client 50 wishes to access.

The motivation and behavioral messages and client questions can also be used in combination with auxiliary devices to fortify the client's messages or questions and provide feedback to the physician or counselor. For example, in the field of weight loss, an electronics scale 38 can be utilized to supply the timely weight of the client to determine if a weight loss or gain has occurred during the reporting period. As shown in FIG. 1, the electronic weight scale is connected to an ordinary telephone line which automatically dials the telephone number associated with the operating system and transmits the weight of a client 50 standing on the scale 38 digitally to the client's program 14 and database 12 for later feedback and analysis in accordance with a weight reduction program.

The scale 38 prevents the client 50 from becoming aware of their day-to-day weight fluctuations. This is consistent with new insights in behavior theory with respect to human motivation which allow an observer or instructor using the computer to review the client's weight periodically through the use of the computer 16 which is at a remote location and can guide the client 50 from time to time based upon the trend or average of their weight, and other devices such as glucose monitoring, blood pressure, heart rate, and cholesterol monitoring.

Research reported by Mori and Morey in 1991 shows that individuals with depression or lower levels of self-esteem are more likely to have a vulnerable or negatively distorted body image (The vulnerable body image of females with feelings of depression, *Journal of Research in Personality*, Vol. 25, 343–354). Furthermore, Nelson and Craighead's 1977 study (Selective recall of positive and negative feedback, self-control behaviors, and depression, *Journal of Abnormal Psychology*, Vol. 86, 379–388), suggests that depressives distort environmental input in such a way that they consistently reach a negative conclusion. Since the depressed person "filters out" a certain amount of positive feedback and is particularly sensitive to negative feedback, it is important to control or limit the frequency of negative feedback (i.e., weight readings or other measures of physical health).

The scale 38 does not have any visible measurement display on its exterior and may be fabricated in the shape of a flat mat by use of strain gauge or other technology or the like for placement in various rooms within a client's dwelling. While not shown in the drawings, it may be envisioned in one application that the scale 38 may be placed in front of a refrigerator door wherein the clients weight is measured at a period of time before the client intakes food.

Another preferred embodiment, shown in FIG. 1, is the use of an olfactory unit 40 which provides a variety of different smells to the client 50 to be used in memory association with the daily telephone interaction. Researchers have successfully trained animals to recognize several different scents and to behave in particular ways when they did—for instance, to lick or chew in expectation of food or water as reported by W. J. Freeman, The physiology of perception, *Scientific American*, 78–85 (February, 1991). A more recent study entitled Olfactory stimuli as context cues in human memory, by A. Cann and D. A. Ross and reported in *American Journal of Psychology*, 91–102 (1989), indicates that an olfactory context cue, when paired with a learning experience, might later be used to produce more efficient performance of the learned behaviors. In fact, the client 50 could carry the proper olfactory stimulus 40 for release at the critical time when performance is finished, thus enhancing the motivational training by providing accessing cues in a way not previously taught in the prior art.

A 1990 study by Frank R. Schab at Yale University ("Odors and the remembrance of things past" reported in *Journal of Experimental Psychology: Learning, Memory and Cognition*, Vol. 16, 648–655), further builds upon the evidence that odors can effectively be used as memory retrieval cues to enhance learning and performance. This is consistent with the "encoding specificity hypothesis" of Tulving & Thompson ("Encoding specificity and retrieval processes in episodic memory," *Psychological Review*, Vol. 80, 352–372 (1973), which states that contextual stimuli (i.e., olfactory cues) are encoded along with target information on learning and serve as memory cues to the target information at retrieval.

Yet another preferred embodiment shown in FIG. 1 incorporates the use of a voice stress analyzer 42, which offers a digital numerical evaluation of the speaker's voice stress level to monitor a client's response during a behavioral motivation reinforcement question. Research by D. O'Hair and M. J. Cody entitled "Gender and vocal stress differences during truthful and deception information sequences," in *Human Relations*, Vol. 40, 1–14 (1987), indicates that voice stress analyzers can be objectively and unobtrusively used to detect vocal stress indicative of deception. If a client 50 knows that his veracity is being tested and that his responses are being analyzed for deception, then there is greater motivation on his part to adhere to the program 14 and hence more rapidly progress towards a particular goal. In addition, commonly encountered self-deception is reduced using this mode.

Yet another preferred embodiment would be a timing means which would be started at the end of a polling question. The timing means would be stopped upon commencement of the client's response and the interval between the end of the question and the commencement of the response would be recorded. While polling is often useful as a means of determining a client's progress, or lack thereof, it is extremely difficult to determine on the basis of traditional methods whether the response is based on an actual occurrence or feeling of the client 50 or whether it is fabricated on the spot for the purpose of providing an answer. In the former case, it is common to think of the attitude as being pre-integrated and crystallized and thus quite stable, whereas in the latter case the response represents an improvisation or may be lacking veracity. By first observing the client's base line or time to respond to questions of known behavior or fact a typical observable pattern emerges. Later his pattern can be compared to the latency in response time to questions of unknown veracity. By measuring and observing the clients latency response interval over a period of time, useful clues and insights emerge which can be used to assess and predict more accurately the degree of crystallization of a person's attitudes and resulting behavior. Such a latency response measuring tool could be utilized in conjunction while a live counselor is working in real time with the client 50.

This embodiment could be utilized in conjunction with any of the cited means herein of communicating polling questions. It is a unique application of determining latency of response to computerized behavioral reinforcement in order to determine the relative degree of crystallization of gradually learned behavior. A further advantage is that such method and apparatus would be transparent from the perspective of the respondent.

Another preferred embodiment incorporates the use of an EEG measuring and recording device 46 which can be used to assess hypnotic susceptibility either in the presence of the client 50 or at some distance by use of a modem for transmitting signals which indicate various brainwave states. Behavior research indicates that there is an increase in alpha activity in the EEG when subjects are exposed to behavioral intervention techniques such as hypnosis, relaxation and meditation. In addition, studies with psychotropic drugs have demonstrated that increased and synchronized alpha activity is a characteristic of all the major tranquilizers. A 1972 study by G. A. Ulett, S. Akpinar and T. M. Itil ("Quantative EEG analysis during hypnosis," *Electroencephalography and Clinical Neurophysiology*, Vol. 33,361–368) reported significant EEG differences between the hypnotic and awake states, with all subjects experiencing increased alpha activity in the hypnotic state. The computer 16 in this mode, receiving and analyzing the signals, can then adjust the intervention to correspond to the client's 50 brainwave state.

Another preferred embodiment shown in FIG. 1, is a computer-driven system for behavioral and motivational reinforcement and guidance which can be applied to various modes of interactive television 44. Its feature of providing customized instruction, learning, and motivational prompts and cues, often where the behavior occurs, provides a unique approach toward directed interactive learning and behavior modification. Using interactive television 44, the computer-driven system converts the traditional broadcast format to a customized "narrowcast," where either classes of learners or individual subscribers are addressed according to their individual issues without specific categories, and each in turn returns individual specific responses to questions or polling, which are then recorded in the client database 12. This application becomes possible because of the larger number of channels available with fiber optic cable facilitating two-way interaction.

It is envisioned that three separate modes of transmission from a computer with interactive television can be utilized:
  (1) fiber optic cable for two-way communication—the computer transmission would appear on the subscriber's screen and he would in turn reply either through a remote control unit or telephone back over the fiber optic cable. The computer would receive his return transmission or reply and note it accordingly in its memory. Periodic and finer tuned follow-up reinforcement could occur via telephone based upon the client's responses over specific time periods.
  (2) coaxial cable—inasmuch as existing coaxial cable systems can transmit hundreds of times more data than a conventional telephone line, the subject computer driven system can transmit learning, motivational guidance and reinforcement to classes of subscribers over existing coaxial cable systems and the subscribers can reply using a remote unit containing computer hardware for reply back over the cable. Alternatively, the remote unit can contain a modem for reply back over a telephone line.
  (3) wireless cable—subscribers without cable would receive the signal via antenna in the case of localized transmission or dish in the case of satellite transmission. The transmission would contain the computer driven learning, motivation and reinforcement. The subscriber would reply via telephone.

In each mode of transmission, subscribers can be reminded of an upcoming transmission via telephone 26 or wireless radio beeper 34 as described herein. Additionally, explanatory brochures can be used with any of the above described interactions as a method of further reinforcing a client 50 toward a particular goal. With today's technology and regulatory infrastructure, programming for interactive television would remain in its current analog form and a special unit, usually a controller box plus remote positioned atop the TV set, would allow the viewer to dip into the data stream and manipulate what appears on the TV screen. With digital and compression technology (compression of up to six or more digital channels into the same bandwidth as one analog channel), a settop box would be used to decode and decompress video and audio signals in real time.

Another preferred embodiment is the use of a computer-based information metering system that uses optical discs 56 as transport and storage media, encrypting to protect data and is metered or by other payment means to permit usage by clients on a pay-per-view or pay per bit of information basis. The encryption-metering device would use digital technology and would be made available through cellular phones, wireless cable transmission, modem, interactive television and CD-ROM. Information would be distributed in encrypted form to users. After the user browses through the menu or index at no charge and selects the item needed, the encryption-metering device will decrypt the information required, record which data was used, by whom and for what issues or subjects, and will permit the user to be billed only for the data used. This information would be unreadable or unlistenable until decrypted and users would be charged based on the number of bits of information selected. A metering chip or computer board would be used to gauge data use just as an electric meter tracks power demand. Information may be retrieved in either full-text audio or image form. A decryption program keeps track of how much data is decoded and can subtract its costs from a prepaid credit stored on a chip as a form of payment. The encryption-metering technology may use a Microsoft Windows® based application or other commercially available software, with familiar graphical interfaces and menuing systems to which users are accustomed, and would be available on a variety of computer platforms.

Another preferred embodiment is the use of CD-ROM or CDI 56 (Compact Disc with Read Only Memory), a high-density storage and delivery medium similar to digital audio compact discs, which stores vast amounts of data in a digital form. Each CD-ROM 56 will hold about 600 megabytes of data, equivalent to a shelf of books almost 100 feet long, with a full text index. CD-ROMs 56 offer the fastest and most convenient way to access material from large data bases. However, most present CD-ROM systems require the user to purchase an entire data base on CD-ROMs. By contrast, the use of encryption technology and metering allows the applicant to distribute each CD-ROM for little or no cost and then charge the user only for the information actually used. The CD-ROMs 56 would be used with standard as well as portable CD-ROM players, allowing users instant access to the material virtually anywhere.

Yet another preferred embodiment is the implementation of a software programming language that is specifically designed for communication and communicating applications. More specifically, such programming language utilizes remote programming which interacts between the server and client computers. By utilizing the network as a vehicle or interpreter for programs, computers are thus able to transmit programs which briefly enter and interact with selected computers on the network for specific purposes. An advantage of this arrangement is that because these transmitted or "remote" programs only are on the network long enough for the computer to compute transmission, the connection only need to be held long enough for the remote program to enter the intended recipient computer, thus effecting considerable savings in transmission costs. One such computer programming language is Telescript, available from General Magic Inc. The software programs which are thus transmitted across networks act as "agents" which contain instructions in the form of behavioral prompts and cues, in addition to educational information. The transmittable software agent programs are capable of providing individual behavioral guidance while minimizing transmission costs. Another advantage is the ability to adapt this programming language to individual tastes, preferences and needs of a large number of individuals. Such software programming language is unique in its application of remote programming software agents. In the case of online systems, one of the possible applications of remote programming language, programmable software agents can be sent out into the network to perform many behavioral tasks, such as providing prompts and cues in a personalized manner allowing each client to obtain desired information while sharing personal experiences which his doctor, psychologist, counselor, teacher or trainer and/or the network at large. Most importantly, messages can be time-sequenced, or filtered as to priority or to be sequenced with the occurrence of specified events. Other messages could be broadcast to various classes of clients on either a narrow or wide format. In instances where messages are not recovered within a given time interval, they can be automatically converted, per the programs' instructions to another medium, such as fax, voice, video, text or a combination thereof in order to provide an alternative means of communication. Alternatively, the message could be delivered to a different or alternative location after the lapse of a given time interval. In instances wherein coordination of medical appointments are necessary for the testing and/or screening of the client's medical affairs, said remote programming can coordinate and remind the client 50 in a timely and convenient manner, and then most importantly, schedule, monitor and reinforce the client's behavior in compliance with necessary medical regimens. In addition, said program can monitor, integrate and order the refilling of prescriptions as necessary. In order to prevent unauthorized ordering of medical prescriptions, the remote programming software contains cryptographic forms of identification. In the United States, the problem of failure to comply with medical requirements has been reported to cost as high as $100 billion.

All of the above succeeds in providing greater time savings and freeing the client of routine tasks which are frustrating, annoying and time-consuming. In other instances, said programming language could be preprogrammed or built into hand-held devices for communication, or stationary PCs or mainframe computers for behavioral guidance. An advantage of this type of computer software is that it is transport independent. It can be delivered by telephone lines, wirelessly, or local or wide area networks, by cable or by other means, allowing the counselor or computer to choose the most timely and best fit for the messages' communication mode.

The significant applications of remote programming can be more fully appreciated wherein several integrated behavioral issues or medical requirements are required to be accomplished, such as where several medications are to be administered at different times of the day in addition to physical activity and individual dietary requirements, thus providing behavioral integration.

Still another preferred embodiment is the use of a CDPD (Cellular Digital Packet Data) Network for the transmission of brief and interactive behavioral prompts and cues. CDPD allows data to be sent over the existing voice cellular network, but with greater bandwidth and lower latency, increased geographic coverage and lower costs than existing packet wireless networks. Users of existing packet data networks experience several-second delays which makes them unstable for two-way interactive communications. By contrast, CDPD usage exhibits subsecond delays allowing more rapid and naturalistic feedback. Power consumption and resulting battery size are reduced with CDPD transmission.

CDPD is suited to behavioral reinforcement and feedback where short text consisting of prompts and cues are appropriate. Additionally, CDPD may be utilized to communicate various physical conditions such as, but not limited to blood pressure, weight, blood sugar, cholesterol, heart rate, medication usage and compliance with medical regimens, all of which are capable of reduction to text, graphical or numerical representation.

Furthermore, CDPD may be utilized to locate clients. The ability to locate individuals within and outside of their usual environments will allow the computer to adjust the length and nature of the behavioral reinforcement in a manner appropriate to the time and setting in which the client is located in order to tailor and integrate the intervention into the client's life. In addition, CDPD may be utilized to notify clients of the arrival of extended messages on other mediums such as E Mail, Voice Mail and FAX.

Still another preferred embodiment shown in FIG. 1, is the use of monographs or "bibliotherapy" 52 as an adjunct to audio, video and in-person feedback. In a study of women in a weight reduction program, the use of written handouts was found to improve levels of self-esteem, assertiveness, attitudes to body size, and self efficacy about weight control. (A. J. Blair, V. J. Lewis, and D. A. Booth, "Response to leaflets about eating and shape by women concerned about their weight," *Behavioral Psychotherapy*, Vol. 20, 279–296 (1992)).

Another preferred embodiment shall summarize the client's data base 12 by way of a publication of individually customized information in the form of reports or graphs, indicating response profiles, educational monographs and tutorials, and other materials necessary for providing motivation and education. By accessing the information stored in the client data base 12, the accumulated personal response profile contained therein provides a means to mix or formulate an individualized or custom printed educational document.

The specific content of this educational document could be adapted to each individual client 50, based upon his education, gender, age, demographic profile, psychological profile, and prior response profiles. This educational document and text would be further formulated according to the individual's present behavioral stage, as will be more fully described below.

Another preferred embodiment is the use of interactive video system 54 to accelerate the learning process. An interactive videodisc 54 system implies that a videodisc player and monitor are interfaced with a microcomputer, thus allowing control of the progression of the program 14. Prior art systems have decreasing capabilities essentially consistent with reduced computer memory. These prior art systems allow proportionally less user control and interactivity. Research shows that with interactive video systems 54, effective learning tends to occur in one-third to one-half of the time required for the same content presented through more traditional approaches (G. Kearsley and J. Frost, March, 1985, "Design factors for successful videodisc-based instruction; *Educational Technology*, 7–13). Positive student responses to the use of interactive video technology (IVT) are reported in the literature (L. Jones and S. G. Smith, March, 1989, "Lights, camera, reaction! The interactive videodisc: A tool for teaching chemistry," *T.H.E. Journal*, 16(7), 78–85) and IVT appears to be particularly well-suited for learning and behavior modification: learning occurs in an environment free from observation and evaluation, users have the freedom to err and to observe the consequences of their decisions, and to use problem-solving strategies to bring about corrected action. Dr. Marion Diamond, at University of California Berkeley, has reported, based on extensive experimentation on rats, that the structure and abilities of the cerebral cortex can be changed throughout life by enriching sensory environments; she concludes that we can actually become smarter as we grow older if we provide our brains with the right encouragement and environment. Indeed, newer learning theories and recent brain research emphasize the importance of an active, empowered learner participating and interacting fully in the creation of his or her own learning.

Figure 3:
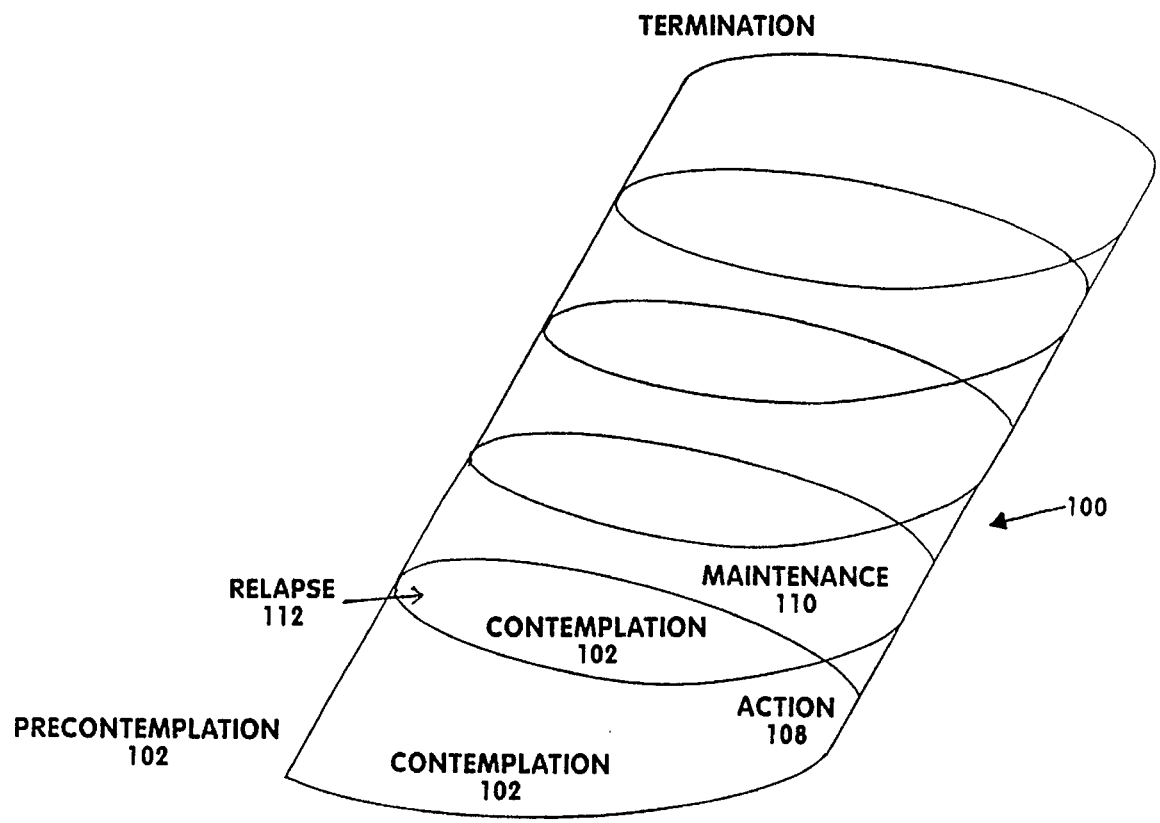
FIG. 3 is a diagram of the spiral model of the stages of change utilized by the computer software program.
Figure 4:
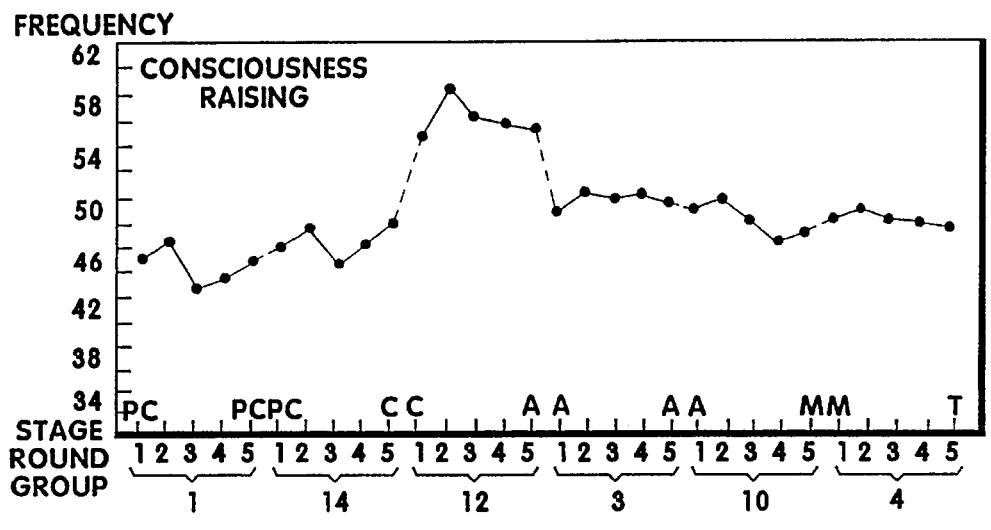
FIG. 4 is a sample graphic representation of consciousness raising for the process of change by profiling actual study groups across the behavioral stages of change.
Figure 5:
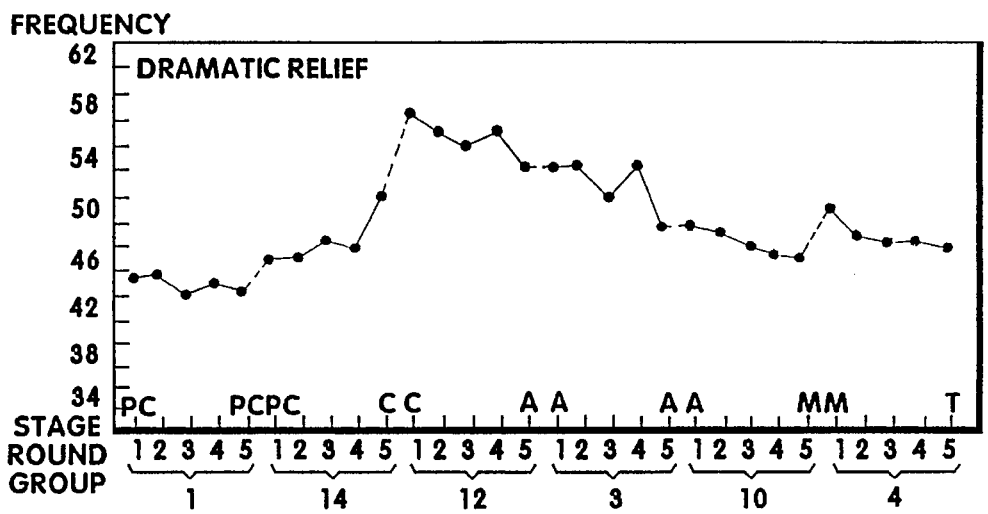
FIG. 5 is a graphic representation of dramatic relief for the process of change by profiling study groups across the behavioral stages of change.
Figure 6:
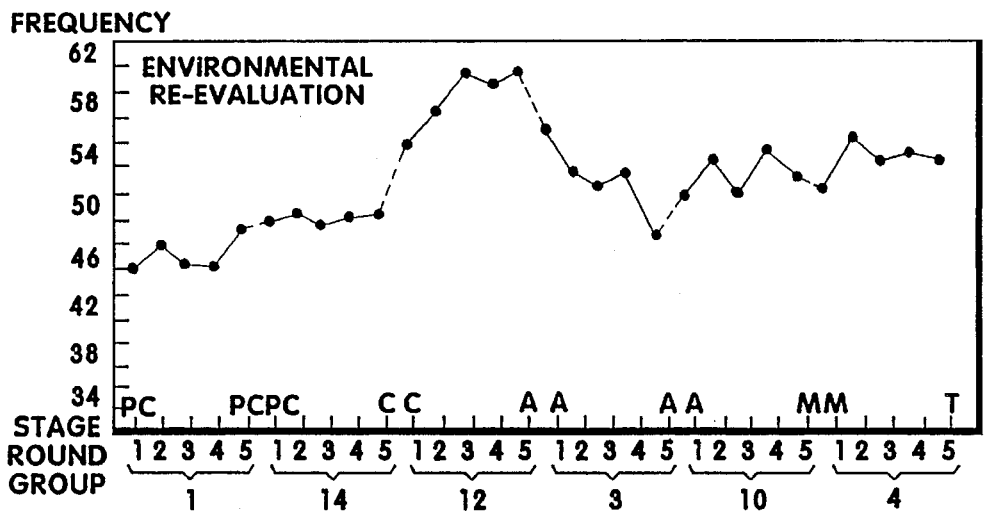
FIG. 6 is a graphic representation of environmental reevaluation for the process of change by profiling study groups across the behavioral stages of change.
Figure 7:
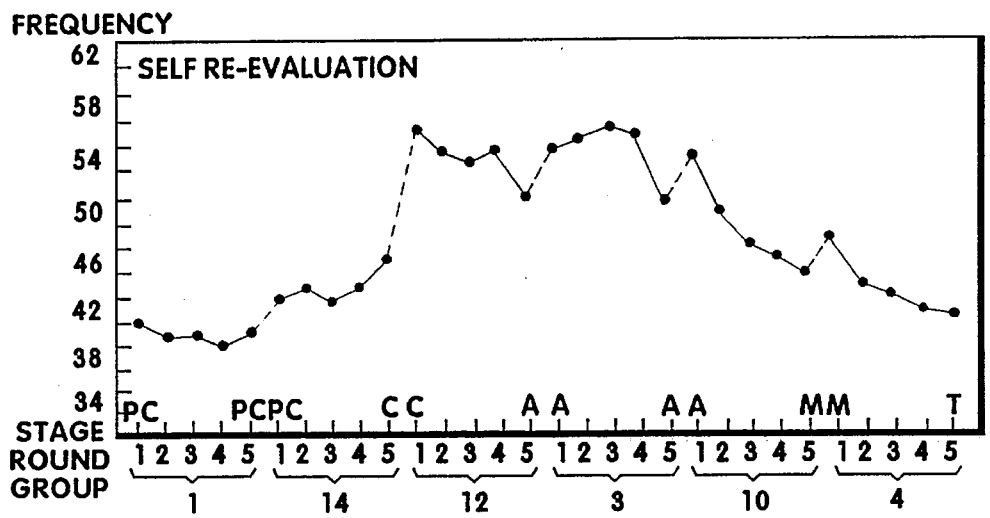
FIG. 7 is a graphic representation of self reevaluation for the process of change by profiling study groups across the behavioral stages of change.
Figure 8:
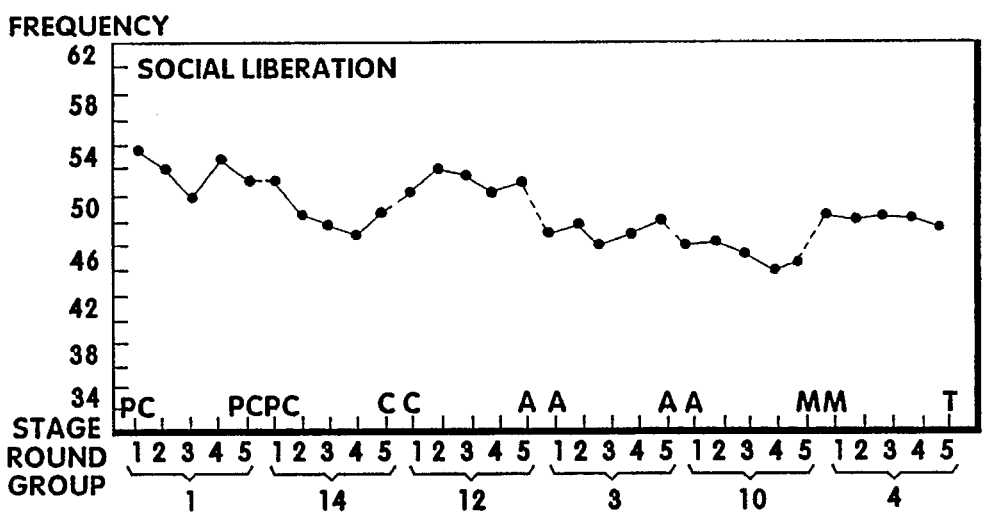
FIG. 8 is a graphic representation of social liberation for the process of change by profiling study groups across the behavioral stages of change.
Figure 9:
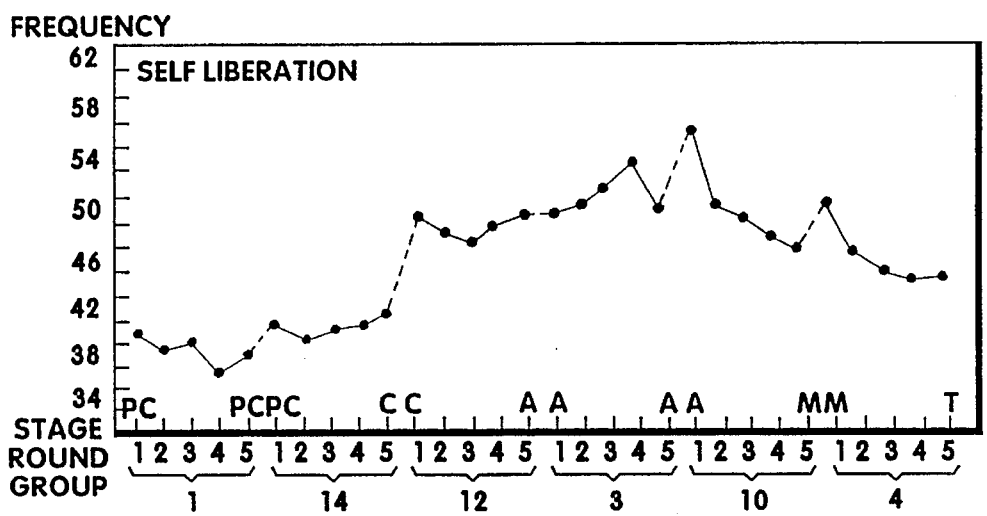
FIG. 9 is a graphic representation of self liberation for the process of change by profiling study groups across the behavioral stages of change.
Figure 10:
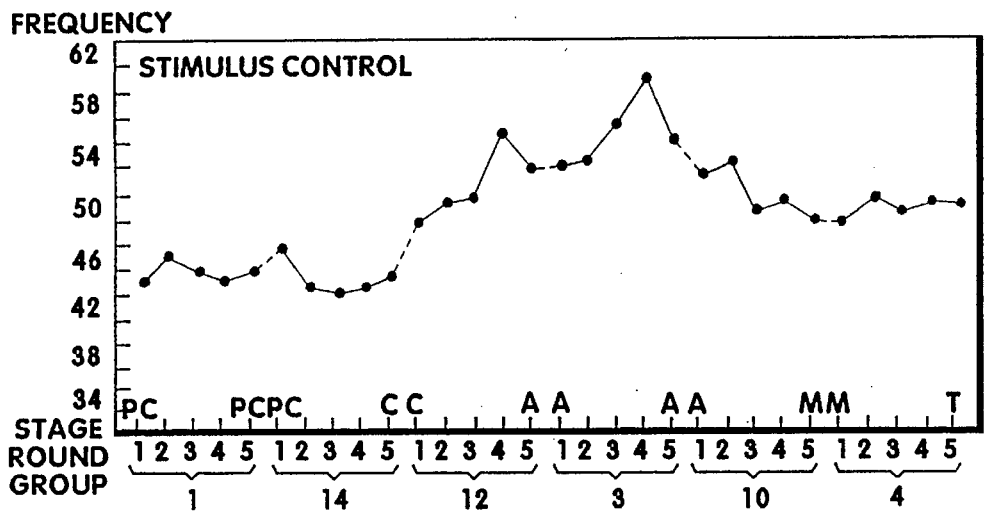
FIG. 10 is a graphic representation of stimulus control for the process of change by profiling study groups across the behavioral stages of change.
Figure 11:
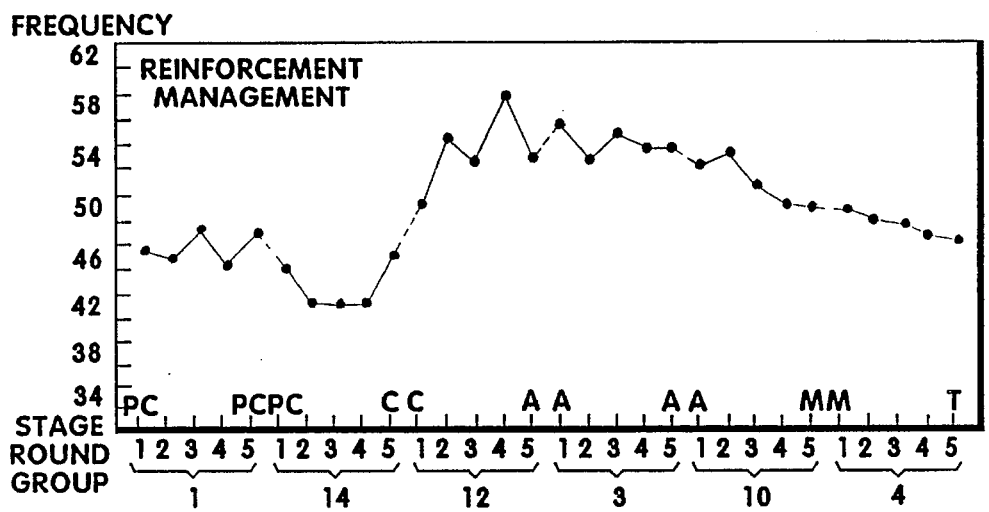
FIG. 11 is a graphic representation of reinforcement management for the process of change by profiling study groups across the behavioral stages of change.
Figure 12:
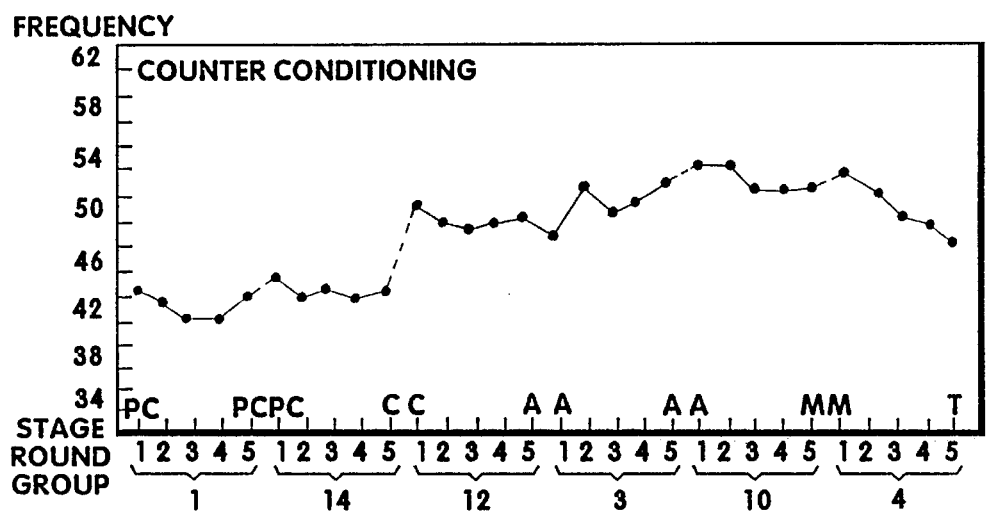
FIG. 12 is a graphic representation of counter conditioning for the process of change by profiling study groups across the behavioral stages of change.
Figure 13:
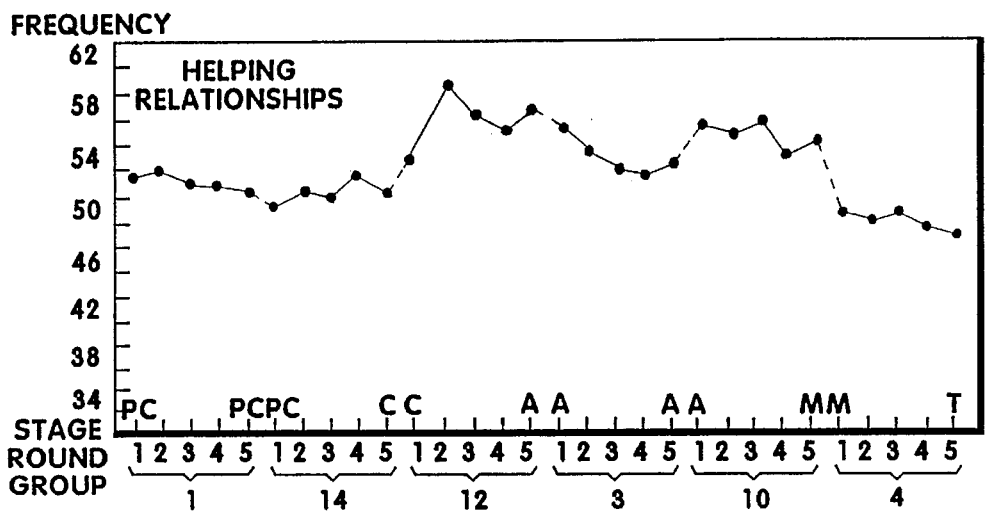
FIG. 13 is a graphic representation of helping relationships for the process of change by profiling study groups across the behavioral stages of change.
Figure 14:
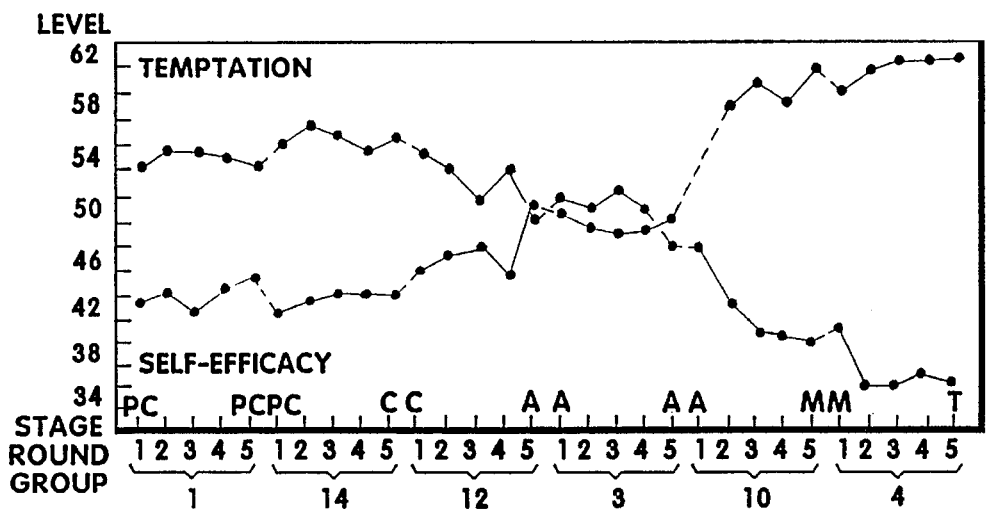
FIG. 14 is a graphic representation of levels of self-efficacy and temptation for the process of change by profiling study groups across the, behavioral stages of change.
Figure 15:
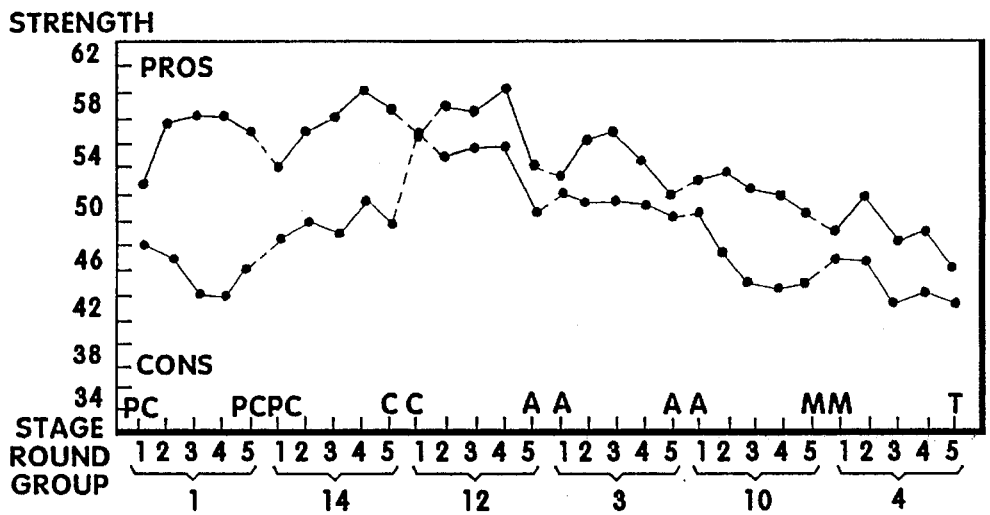
FIG. 15 is a graphic representation of the strength of the pros and cons for the process of change by profiling study groups across the behavioral stages of change.

As shown in FIG. 3 and as reported by Prochaska and DiClemente (1984), the preferred embodiment is the application of the spiral or staged model of change 100 incorporated within the client program 14 as a multifaceted behavioral modification program. Researchers James Prochaska, Carlo DiClemente and John Norcross have created a spiral model of behavioral change 100 which conceptualizes the process of behavioral change in a client 50 in the context of a non-linear framework. Their research revealed that relapse is the rule rather than the exception among individuals with addictive behavior patterns. Therefore, by reframing relapse as a normal stage in the process, their model suggests that relapse is merely a temporary setback and that most relapsers do not regress all the way back to where they began. Instead, they use relapse as a learning experience from which to attain newer heights and move forward, in a spiral process change.

The spiral model of change 100, as shown in FIG. 3, depicts the cycle of change as consisting of six (6) distinct behavioral stages. Therefore, the client program 14 will be directed to moving the client 50 from one of the following six and variant stages of behavioral change 100, which are: precontemplation stage 102; contemplation stage 104; preparation stage 106 (not shown); action stage 108; maintenance stage 110; and relapse stage 112.

Prochaska, et al., have found that each of these six (6) behavioral stages is characterized by a set of specific behavior patterns. Precontemplation 102 is the behavioral stage 100 in which people are not intending to change their behavior. Many individuals or clients in this stage are unaware or underaware that they have a problem. Typically, their families, friends, neighbors or employers are well aware that there are problems. Usually the client 50 in this behavioral stage 100 feels coerced into changing. He may feel pressured by a spouse who threatens to leave; an employer who threatens to fire him; parents who threaten to disown him; or courts who threaten to punish him. He may even demonstrate change as long as the pressure is on. Once the pressure is off, however, research has shown that he quickly returns to his old ways.

The contemplation stage 104 is the behavioral stage 100 in which one becomes aware that a problem exists. In this behavioral stage 100, the client 50 seriously thinks about overcoming his problems. Although contemplators think about change, they have not made commitments to take action. Research has typically shown that clients in this behavioral stage 100 remain stuck in the contemplation stage 104 for long periods of time.

The preparation stage 106 is that behavioral stage 100 in which the client 50 begins to start the modification of his behavior, which is directly followed by the action stage 108, wherein he is modifying his behavior, experiences, and/or environment in order to overcome his behavioral problem. The action stage 108 is the busiest stage and requires considerable commitment of time and energy. Behavioral changes made in the action stage 108 tend to be most visible and receive the greatest recognition from others.

The maintenance stage 110 is the time in which one works to prevent relapse and continue the gains made during the action stage 108. Traditionally, the maintenance stage 110 was viewed as a static stage. However, research has shown that the maintenance stage 110 is not an absence of change, but a continuation of behavioral change. Unfortunately, with some of the most common behavior problems, the client 50 will not successfully maintain his gains the first time through the stages of change 100. By way of example but not of limitation, smokers who are successfully self changers make an average of three to four action attempts before they become long-term maintainers. Since the relapse stage 112 is the rule rather than the exception, in solving such common problems as alcohol abuse, smoking, and weight control, the client 50 will demonstrate a behavior along the spiral model of change 100.

In the spiral pattern, the client 50 will progress from contemplation 104 to preparation 106 (not shown), to action 108, to maintenance 110, but most individuals will go back to the relapse stage 112. During the relapse stage 112, the client 50 will regress to an earlier stage. Some relapsers feel like failures: embarrassed, ashamed, and/or guilty. These individuals become demoralized and do not want to think about change. As a result, they return to the precontemplation stage 102.

Therefore, it is an object of the client program 14 in this embodiment to utilize the client's data base 12 and computer 16 to determine where the client is on the stage model of change 100, and from there—through interactive telecommunications—move the client 50 from one stage to the next stage, until the maintenance stage 110 is achieved and maintained, and the targeted problem behavior is eliminated. The likelihood of successful change appears to be directly linked to an individual's position on the spiral (i.e., the particular stage within the model). Indeed, the progress made by patients as a result of professional interventions tends to be a function of the stage 100 they are in at the start of treatment.

By way of example but not of limitation, the client program 14 and client data base 12 will ask the client 50 if he currently has a problem or has engaged in a desired positive behavior. If he reports an undesired status and does not intend to change in the next six months, he will be categorized as being in the precontemplation stage 102. If the client 50, however, intends to change within the next six months, then he is categorized as being in the contemplation stage 104. For the preparation stage 106, the client 50 indicates that he is planning to change in the next month or have made some changes, but was not at a particular criterion. By way of example but not of limitation, an exercise program wherein the client 50 was performing a minimum of 20 minutes three times a week would be considered in the preparation stage 106. A client 50 in the action stage 108 would have reached a particular criterion, such as quitting smoking or cocaine, within the past six months. A client 50 in the maintenance stage 110 has reached the criterion more than six months before the client data base 12 was instituted. The timing criteria varies, but most often is the same for all behavioral problems, wherein a 12-month criterion is typically appropriate for assessing action and intentions to be taken.

Once the behavioral stage 100 has been categorized from the client data base 12, the stages of change 114 are utilized by the client program 14 at the critical temporal dimension that allows the client program 14 to move the client 50 from one behavioral stage 100 to another. In the spiral or stage model of change 100, these processes of change 114 are the independent variables that assess how the client 50 is to proceed to change behaviors.

Change processes 114 are covert and overt activities that individuals use to modify problem behaviors. In the past, these independent variables were used by therapists, clients, or individuals attempting to change without therapy. Hereafter, these processes 114 will be used by the client program 14 in order to change the client's behavior stage 100.

As shown in Table I below, there are 14 processes of change 114 that have received the most theoretical and empirical support in research to date. A common set of change processes 114 has been clearly identified across such diverse problem areas as the psychological distress syndrome (a combination of anxiety, depression and lowered self-esteem) and smoking and weight control.

Table 1. Processes of Change

116. Consciousness raising
118. Self-reevaluation
120. Self-liberation
122. Counterconditioning
124. Stimulus control
126. Contingency management
128. Helping relationships
130. Dramatic relief
132. Environmental reevaluation
134. Social liberation
136. Self-efficacy
138. Temptations to relapse
140. Decisional pros
142. Decisional cons The following are some examples that demonstrate the mechanism of the aforementioned processes of change 114:

The consciousness raising process 116 is the process wherein the client 50 increases information about self and problem: his observations, confrontations, interpretations and bibliotherapy;

the self-realization process 118 is how the client assesses how he feels or thinks about himself with respect to a problem: value clarification, imagery, and corrective emotional experience;

the self-liberation stage 120 is the process the client chooses and commits to act or believe in his ability to change: decision-making therapy, New Year's resolutions, logotherapy techniques, and commitment enhancing techniques;

the counterconditioning stage 122 is the process wherein the client substitutes alternatives for problem anxiety related behaviors, e.g., relaxation, desensitization, assertion and positive self-statements;

the stimulus control stage 124 is the process where the client actively avoids stimuli that may elicit problem behaviors by: adding stimuli that encourage alternative behaviors; restructuring one's environment, e.g., removing alcohol or fattening foods; avoiding high risk cues; and using fading techniques;

the contingency management stage 126 is the process used by the client to reward himself or is rewarded by another for making changes: contingency contracts; overt and covert reinforcement; and self-reward;

the helping relationships stage 128 is the process enlisted by the client for being open and trusting about problems with someone who cares: therapeutic alliance; social support; and self-help groups;

the dramatic relief stage 130 is the process where the client experiences and expresses his feelings about his problems and solutions through psychodrama; grieving losses; and role playing;

the environmental reevaluation stage 132 is the process utilized by the client to assess how his problems affect the physical environment, utilizing empathy training and documentaries; and the social liberation stage 134 is the process of change utilized by the client as an alternative to nonproblem behaviors available in society: advocating for the rights of the repressed; empowering; and policy interventions.

Furthermore, the dynamic topology of these 14 newly derived patterns of change processes 114, which has been tracked by researchers, now graphically describes individual change of behavior in both the self- and professionally-managed approaches to the realization of personal goals. As shown in FIGS. 4 through 13, these graphical representations, as reported in Patterns of Change: Dynamic Typology Applied to Smoking Cessation, Prochaska et al (1991), are significant inasmuch as they are the first attempts to depict the curves illustrating the dynamics of growth and development throughout each individual process 114 over a measured and relevant period of time.

Since the dynamics of these change processes 114 or variables have now been graphically depicted based upon actual case studies, it is now possible for the first to implement the derived structure into a template or dynamic model utilizing computer software such as but not limited to: neural networks and knowledge-based expert systems. Utilizing computer software techniques, it is now possible to reduce the topology of these curves and graphical representations into reinforcement commands in the form of prompts and cues for behavior and motivational learning and reinforcement.

By knowing the shape of the behavior of a large number of individuals over a given temporal or time interval, it becomes possible to direct, shape and model individual behavior through automated computer administration and management, as opposed to the ineffective means of only interacting for a short time with a self-help book or a psychotherapist.

Therefore, client program 14, by utilizing the client data base 12, will be able to provide to the client 50 direction and reinforcement targeted to his exact position on the graphical representation, model or template shown in FIGS. 4 through 13. In doing so, the client 50 is able to be more accurately directed across a continuum or process towards a predetermined goal. The application of these performance curves through computer administration, uniquely act as an automatic guidance control for performance. In addition, he is able to more closely approximate and synchronize behavioral reinforcement and guidance to actual behavior or lack thereof, within the same approximate time frame that the behavior or lack thereof should occur. This is possible because guidance is transmitted to site of performance where the client 50 can integrate it immediately into his life.

By integrating the processes and stages of change as outlined by Prochaska et al., to create a multifaceted and multidimensional treatment system, this system tailors particular behavioral interventions accompanied by facts of the subject invention and its embodiments to clients in a customized manner consistent with the location they are in within each cycle and stage within the aforesaid spiral process as shown in FIG. 3. For example, during the contemplation stage 104, individuals are most open to consciousness-raising techniques and are more likely to use bibliotherapy and other feedback and reinforcement educational techniques. During the action stage 108 clients need help with behavioral processes such as counter-conditioning and stimulus control to prevent relapse. During the maintenance stage 110, there is a continued emphasis on coping skills as well as a focus on improving self-efficacy levels. In some cases, the same intervention or technique may be used across several different stages of change, but with varying degrees of intensity and/or frequency. There are numerous research studies which support the notion that matching therapy programs and processes to the client's stage of change 100, as conceptualized by Prochaska et al., will better serve the majority of clients.

By way of example but not of limitation, an online and/or CD-ROM multimedia or video game with an ascending spiral interaction or script would be used as part of the program 14. Clients 50 would be consciously or unconsciously imprinting the spiral image in their minds each time they played the game, acting out or visualizing the process of contemplation 104, preparation 102, action 108, maintenance 110 and relapse 112, and then starting again over the same cycle, thereby providing themselves with a strong sense of dramatic victory without personal or physical danger. The lessons learned, such as problem solving, pattern recognition, quick thinking, resource management and reasoned judgment, could then be gradually adopted with the client's life. For online users it may be envisioned that a settop box would be used to render interactive 3D graphics in real time.

These features and their advantages in use will be more particularly appreciated when reviewing the following method of the present invention used to move a client 50 from one behavioral stage 100 to the next. In application, the client 50 is given a Stages Of Change Questionnaire, a 32-item assessment instrument or the like such as reported in "Stages of Change in Psychotherapy: A Follow-up Report," *Psychotherapy*, Vol. 26, #4 (1989), 502–503, which measures the aforementioned behavioral stages 100. This particular instrument was developed and validated with a sample of 150 clients presenting for outpatient psychotherapy, and replicated and cross-validated with another sample of 350 clients presenting for treatment. The clients responded to a weight control version of this scale, using a five point Likert format in which 1 equals "strongly disagree" and 5 equals "strongly agree." An example of such an assessment instrument is the 32-item Stages of Change Questionnaire is attached hereto as Appendix A.

By utilizing the Stages of Change Questionnaire, the client 50 is classified into the behavioral stage 100 where he belongs for the given behavior that is to be modified.

Table II shows one correlation used by the client program 14 for the process of change 114 for a given behavioral stage 100.

TABLE II

Correlation Between Behavioral Stage and Selected Processes of Change

| Behavioral Stage | Process of Change |
| --- | --- |
| 1. Contemplation | Intervention<br>Consciousness raising<br>Dramatic relief |
| 2. Preparation | Self reevaluation<br>Environmental reevaluation<br>Helping relationships |
| 3. Action | Self liberation<br>Counterconditioning<br>Stimulus control<br>Reinforcement management<br>Helping relationships |
| 4. Maintenance | Counterconditioning<br>Stimulus control |

Table III below gives definitions for the different processes of change 114 that will be associated with each behavioral stage 100 so that the client program 14, through use of the computer program 16, will be the basis of the interactive dialogue used in the client program 14 with client 50.

TABLE III

Stages of the Process of Change

| Processes | Definition: Interventions |
| --- | --- |
| 116. Consciousness raising | Increasing information about self and problem: observations; confrontation; interpretations; bibliotherapy. |
| 118. Self-reevaluation | Assessing how one feels and thinks about oneself with respect to a problem: value clarification; imagery; corrective emotional experience. |
| 120. Self-liberation | Choosing and commitment to act or believe in ability to change: decision-making therapy; New Year's resolutions; logotherapy techniques; commitment enhancing techniques. |
| 122. Counterconditioning | Substituting alternatives for problem anxiety related behaviors: relaxation; desensitization; assertion; positive self-statements. |
| 124. Stimulus control | Avoiding stimuli that elicit problem behaviors: adding stimuli that encourage alternative behaviors; restructuring one's environment (e.g., removing alcohol or fattening foods) avoiding high risk cues; fading techniques. |
| 126. Contingency management | Rewarding oneself or being rewarded by other for making changes: contingency contracts; overt and covert reinforcement; self-reward. |
| 128. Helping relationships | Being open and trusting about problems with someone who cares; therapeutic alliance; social support; self-help groups. |
| 130. Dramatic relief | Experiencing and expressing feelings about one's problems and solutions; psychodrama; grieving losses; role playing. |
| 132. Environmental reevaluation | Assessing how one's problems affects physical environment: empathy training; documentaries. |
| 134. Social liberation | Increasing alternatives for nonproblem behaviors available in society: advocating for rights of repressed; empowering; policy interventions. |

By way of example but not of limitation, the following schematic represents a format that may be utilized by the client program 14 for development of a dialogue for use in smoking cessation using the aforementioned processes of change 114 shown in Table III in association with stage model of behavioral change 100 shown in Table II.

EXAMPLE I

Format Model for Smoking Cessation

1. Greeting
2. Enter password: computer retrieves user's computer file and extends personal welcome
3. Determine Prior Stage of Change (accessed from stores memory):
   A. If prior stage=contemplation, determine if quit date has been previously set:

(i) If quit date not set, ask # cigarettes smoked
  (a) If #>0→GO TO CONTEMPLATION DIALOGUE (Step 4.B)
  (b) If #=0, determine quit date→GO TO ACTION DIALOGUE (Step 4.D)
(ii) If quit date was set, determine if current date is day before or day of quitting:
  (a) If day before quit date→GO TO DAY BEFORE DIALOGUE (Step 4.C)
  (b) If day of quitting→GO TO DAY OF QUITTING DIALOGUE (Step 4.C)
  (c) If neither, ask # cigarettes smoked
    (1) If #>0→GO TO CONTEMPLATION DIALOGUE (Step 4.B)
    (2) If #=0→GO TO ACTION DIALOGUE (Step 4.D)

B. If prior stage=action, ask if they have smoked any cigarettes:
(i) If no→GO TO ACTION DIALOGUE (Step 4.D)
(ii) If yes, determine if this is a lapse or relapse:
  (a) If lapse, identify circumstances, recommend strategies for the future, and→GO TO ACTION DIALOGUE (Step 4.D)
  (b) If relapse, identify circumstances, and determine stage:
    (1) If precontemplation→GO TO PRECONTEMPLATION DIALOGUE (Step 4.A)
    (2) If contemplation→GO TO CONTEMPLATION DIALOGUE (Step 4.B)

C. If prior stage=precontemplation, evaluate current stage
(i) If precontemplation→GO TO PRECONTEMPLATION DIALOGUE (Step 4.A)
(ii) If contemplation, provide feedback→GO TO CONTEMPLATION DIALOGUE (Step 4.B)
(iii) If action, provide feedback determine quit date and →GO TO ACTION DIALOGUE (Step 4.D)

4. Specific Dialogues
  A. Precontemplation
  briefly inform about health effects of smoking and benefits o quitting
  suggest importance of another try
  recommend continued participation
  reinforce notion of physician as caring and system acting on their behalf
  determine if interested in quitting
    If interested, provide feedback, set stage for contemplation→GO TO CLOSING
    If not interested, provide feedback→GO TO CLOSING
  B. Contemplation
  inform about adverse effects of smoking
  inform about benefits of quitting
  identify reasons for potential difficulty in quitting (emphasize reasons that have given smoker difficulty in the past and provide strategies to deal with them)
  address common questions and concerns
  review reasons why caller smokes
  describe reasons to quit and identify those most important to the individual user
  increase awareness of behavioral patterns around caller's smoking
  deal with concerns of changes in sense of self
  determine if ready for action
    If not ready, identify reasons, provide suggestions for overcoming barriers→GO TO CLOSING
    If ready, determine method desired to quit, attempt to set quit date, provide feedback→GO TO CLOSING C. Day before Quitting and Day of Quitting
provide feedback, suggestions, support
inform of changes that will take place
remind individual of reasons for quitting→GO TO CLOSING D. Action
reinforce importance of caller's own efforts
reinforce notion of physician as caring and system acting on patient's behalf
suggest quitter reward themselves
reinforce positive feedback that caller receives from others
suggest removing tempting stimuli
suggest placing barriers to relapse
identify withdrawal symptoms and methods to deal with them 4. Closing
brief positive reinforcement
restate benefits of smoking cessation
remind about next conversation Additionally by way of example but not of limitation, the following schematic represents a format which may be utilized in the client program 14 as a dialogue for exercise participation for the elderly, once again using the processes of change 114 shown in Table III in association with the stage model of behavioral change 100 shown in Table II.

EXAMPLE II

Format Model for Exercise Participation for the Elderly

1. Greeting
2. Enter password: computer retrieves user's computer file and extends personal salutation
3. Determine Current Activity Level and Stage of Adoption:
  A. # of walks in the past week
  B. # of minutes total spend walking in the past week
  Precontemplation/Contemplation=0 walks→GO TO 4A (unless in Preparation within past month)→GO TO 4B
  Preparation—102 walks and≧10 minutes per walk→GO TO 4B
  Action/Maintenance—≧3 walks and≧60 minutes→GO TO 4C
4. Dialogues Specific to Each Stage of Adoption
  A. Precontemplation/Contemplation
  inform about benefits of walking and risks of inactivity
  determine if interest in starting to walk and, if not (e.g., a precontemplator), suggest user consider walking and→GO TO 6
  if interested in starting to walk (e.g., a contemplator), continue
  if user set a "start date" previously but failed to start, then identify barriers to starting and respond to them; enhance self-efficacy to try again
  negotiate a "start date"
  select type of walking
  negotiate duration of walk
  advice on how to begin walking B. Preparation compare answers to questions in #3 to previously agreed upon goal if user reached goal, congratulate; suggest self-reward if appropriate if user did not reach goal, inquire about barriers and respond to them; enhance self-efficacy to try again negotiate new goal (# walks and/or duration of walks)

inquire about physical problems related to the walking and address them

C. Action/Maintenance compare answers to questions in #3 to previously agreed upon goal if user reached/maintained goal, congratulate; suggest self-reward if appropriate if user did not reach goal level of walking, inquire about barriers and respond to them; enhance self-efficacy to try again inquire about physical problems related to the walking and address them 5. Advice about weather
6. Closing summarize goal negotiated brief positive reinforcement restate benefits of walking state that conversation content will be communicated to the elder's physician remind about tomorrow's conversation By way of example but not of limitation, attached hereto as Appendix B is a monologue incorporating the embodiment of the above-described format for behavioral modification method of the present invention. The monologue comprises moving a client 50 (in this case, a middle-aged woman) from the contemplation stage 104 to the action stage 108 using a selection of the aforementioned stages of change 114 directed to an exercise program. In this example, the receiving and transmission means between the client program 14 and client 50 is through use of both a telephone network 24 and two-way interactive message device 36.

Additionally, the use, separately or in combination, of multiple media such as audio, motion video, still images, graphics, animation, and text may be used to enhance the ability of the user to absorb and learn new information and make corresponding behavioral modifications.

It is also envisioned that the above described devices may be used in conjunction with personalized monographs 52 by one-on-one interviews to develop a client database to improve and enhance the audio, video and in-person aforementioned behavior modification techniques.

Another preferred embodiment consists of the application of a behavioral principle applied to the process of change directed to the aforementioned pros and cons processes for the appropriate targeting or matching of the content of prompts and cues used for reinforcement and educational insight including, but not limited to, polling and broadcasts or transmissions by all prior methods previously cited herein. In addition, this principle in association with delivering pro and con messages, may be applied to the formulation and delivery of written material, publications and text, including all screen based media and CD-ROM's 56, in order to formulate and customize or personalize targeted guidance to each client's individual issues.

By use or application commercially through the herein computerized system, this principle is applied in a unique and novel manner for the design and construction of the content of behavioral dialogues. The unique feature of this embodiment is the adaption of a principle for the prediction of human behavioral change to a computerized application which incorporates and cross references all prior embodiments herein. This principle reduces the process of changing from one behavioral stage to the next into a simple set of mathematical relationships by utilizing the aforementioned pros and cons of the process of change 114 as follows:

Progression from precontemplation (PC) to action (A) is a function of approximately a 1-standard-deviation (SD) increase in the number of pro messages for a healthy behavior change ($PROS_H$). The formula for this principle is the following:

$$PC \rightarrow A \cong 1SD \uparrow PROS_H$$

The corollary to this principle is the following: Progression from precontemplation to action is a function of approximately a 1-standard-deviation increase in the number of con messages for not making a healthy behavior change ($CONS_{UNH}$). Not making a healthy change includes failure to cease an unhealthy behavior and failure to acquire a healthy behavior. This corollary is a mirror image of the original principle. The formula for this corollary is the following:

$$PC \rightarrow A \cong 1SD \uparrow CONS_{UNH}$$

Progression from precontemplation to action is a function of approximately a one half of a standard deviation decrease in the con messages for a healthy behavior change ($CONS_H$). The formula for this principle is the following:

$$PC \rightarrow A \cong 0.5SD \downarrow CONS_H$$

The corollary to this principle is as follows: Progression from precontemplation to action is a function of approximately a one-half of a standard deviation decrease in the pro messages for not making a healthy behavior change ($PROS_{UNH}$) The corollary is a mirror image of the weak principle. The formula for it is the following:

$$PC \rightarrow A \cong 0.5SD \downarrow PROS_{UNH}$$

The proven predictive ability of these formulae allow counselors, physicians, trainers, teachers, supervisors, psychotherapists and all other individuals responsible for training, treating or otherwise administering the guidance of individuals to place each person in one of the several stages or states at each different point in time and to then administer appropriate motivation and reinforcement by the number of pro and con messages delivered, in order to move said individual to a different behavioral stage.

All of this is accomplished herein by providing a template or staging algorithm for optimal matching of the content of each interactive message or dialogue to the client. Similarly, written or screen based text is appropriately matched to each individual for learning and reinforcement.

Due to the complexity of the numerous variables consisting of stages, processes and levels of behavioral change dynamics in schemata such as the trans theoretical or staged process model 100 as described in its present form in cited references, the computerized management and transmission of behavioral guidance embodying all of these newly discovered principles utilizing the transtheoretical or staged model to the site where behavior occurs is a unique application and advancement of the prior art.

In another preferred embodiment, the client program 14 may be directed by a master server system which utilizes the afore-described behavioral modification method. The master server at all times tracks the whereabouts of the client 50 using any of the variety of aforementioned locator means, including but not limited to, the use of an "800" number with caller I.D. where available which is manually or automatically dialed from the current client location, and has the additional capability of selecting a particular platform or subsidiary server corresponding to a behavior which is to be modified or desired communication mode, depending on the time of day and activities of the client 50, and the stage 100 at which the client 50 is in according to his behavioral modification program.

In the preferred embodiment, the master server system uses a knowledge base or expert system known in the art of computer programming for the selection of the appropriate platform corresponding to a behavioral area and intervention technique, or specific communication mode, thereby eliminating the need of a psychologist or therapist in making the decisions on guiding the client 50 to different platform servers corresponding to behavioral component areas such as weight, addiction, volitional or motivation problems or communication modes. The master server selects the appropriate platform based on the historic data, derived from the answers to the prompts and cues, that is stored within the client database 12. In addition, the master server acting in its decision-making capacity, recognizes and differentiates between the stages, processes and number of relapse cycles experienced by each individual client, thereby adjusting the formulation of content and selecting appropriate reinforcement in order that it will continue to be fresh, novel and appropriate. Therefore, by incorporating a master server system in association with the behavioral modification method of the present invention, a variety of platform servers corresponding to different behaviors and/or communication modes can be chosen to serve a particular client 50 on one individual platform server or more particularly, modifying one type of behavior through one or more communication modes at a time. Thus, there is herein described a system for addressing a plurality of behavioral areas and communication modes without the intervention of a psychotherapist, counselor or therapist.

While the invention has been described in complete detail and pictorially shown in the accompanying drawings it is not to be limited to such details, since many changes and modifications may be made in the invention without departing from the spirit and scope thereof. For example, a variety of emerging telecommunication technologies provide varied platforms to transmit behavioral motivation and reinforcement. Some of these devices include: enhanced telephones containing LCD display screens for the representation of data and graphs; personal communication networks which use low power digital radio; palm-top calculators which received satellite transmissions as part of a nationwide network; wireless radio networks which exchange data on a national basis; digital cellular phones which signal their whereabouts on a continuous basis in order that their owner may be located anywhere in the world through linkage to a satellite network; and personal digital assistants (PDA) which can receive data, organize it, monitor the client's activities, give reminders and then communicate via an internal modem as to the client's compliance with a central mainframe computer. Also, the application of the spiral or staged model of change may be applied to all of the behavioral modification programs heretofore discussed, in addition to other areas requiring continuing behavioral reinforcement.

Still another embodiment is that of a means for initiating a behavioral contract between the client 50 and the physician, counselor or trainer. The findings in counseling and behavioral research indicate that it is beneficial to encourage the client 50 to make clear statements committing himself to a course of action. For example, in a smoking discussion, the counselor clearly states the opinion that the client 50 ought to stop smoking and then encourages a verbal commitment from the client 50 to a specific day and hour when he or she will stop smoking. Alternatively, a physician elicits a commitment from a patient to engage in a given number of specific exercises per week and the regular taking of medication.

This model of behavioral contracting has been used in both verbal and written forms signed by the patient in various therapies and has been tested on a variety of behaviors as reported by I. L. Janis in *Counseling on Personal Decisions, Theory and Research on Short Term Helping Relationships*, New Haven, Yale University Press (1982) and by V. C. Li, Y. J. Kim, and C. E. Ewart et al as reported in "Effects of Physician Counseling on the Smoking Behavior of Asbestos Workers, *Preventive Medicine*, 13:462–476 (1973). Physicians' success in eliciting this commitment was shown to be closely related to patient compliance, as reported by Bertram Stoffelmayr, et al in "Facilitating Patient Participation: The Doctor-Patient Encounter," *Primary Care*, 16:1, 269–70 (1989). Therefore, the making of direct verbal statements in the form of commitments by the patient is an important form of behavior modification for compliance.

Therefore, the client program may request that the client 50 make a verbal statement as to his proximate and distal goals based upon various prompts and cues received by the system described herein. The client 50 is asked to press a button on the keypad or other response device when he is about to state his goals. Upon completion of his verbal commitment, he then presses the button on the keypad again to signal that he has finished. Upon giving his first signal that he will state his commitment, his voice is recorded and stored in the device's memory. After a discrete interval, perhaps a week or more, his commitment in his own voice is played to him without prior warning following relevant prompts and cues in order to remind him forcefully in his own voice of his undertaking. The combined effect of replaying the commitment without warning after a discrete interval is one of novelty and surprise which in turn reinforces the client 50 of his original intention at an earlier time. By combining the instant invention and its ability to record and store verbal data, with proven behavioral findings, the state of the art is extended in a novel and unique manner.

Still another embodiment would be video conferencing. Motivational guidance and reinforcement can be provided by the use of a computer 16 connected to a telephone line by providing the client 50 with one or more video compression boards wherein he can receive compressed video transmissions which are synchronized to sound in addition to text. The personalized transmission can be either in real time or delayed transmission. In instances where delayed transmission is utilized, it may be provided from various storage media such as CD-1, CD-ROM and video tape (VCR).

The advantage of providing video images to clients with a personal computer is that the client 50 can experience the presence of his health care provider or counselor for greater effect and impact in behavioral guidance. In instances where the client 50 receives real time transmissions, he may interact with the health care provider immediately. By contrast, in instances where the client 50 receives recorded transmissions, he may respond and his responses can be noted by the host computer. Alternatively, the client 50 can call a voice mailbox and ask individual questions for later response by the physician or counselor.

By the addition of a video camera to the client 50's personal computer, the health care provider can observe the client 50 and record his responses. Transmission can be over ATM, ISDN lines or via MODEM over analog telephone lines with appropriate signal compression. Configurations commercially available, such as INTEL, Personal Conferencing Video Systems, among others, provide the necessary components for this extension of the art.

Yet another embodiment would be the utilization of the numerous configurations of mainframe servers currently under development for interactive multimedia transmission for enabling thousands of individual customers to order video-on-demand simultaneously or home shopping. This technology configuration of a large central mainframe containing thousands of microprocessors would be particularly applicable to clinics and local or regional hospitals. Each hospital may currently serve a population in its locality of between 50,000 and 200,000 individuals. Therefore, the hospital of the future, by using the above-described interactive behavioral modification program, will place increasing emphasis on home health care.

Yet another preferred embodiment would be an interconnected server similar to the one envisaged by Microsoft which connects a large number of "motherboards" similar to those in a PC and runs them simultaneously with custom software. Likewise, large server configurations can be adapted to small retail chains for ownership and operation at one central location, interconnecting all of its stores with its customers via cable or telephone for shopping purposes.

Alternatively and yet another configuration would be for a large hospital server to rent or share space with local clinics, psychotherapists and other health care providers. Prescriptions at the local pharmacy could be made part of this health delivery system wherein patient consumption of medication could be monitored and refills ordered based upon consumption profiles recorded in the data base and through polling questions administered daily. Further, local pharmacy personnel could be utilized to further explain and educate patients on the precise manner in which to administer prescribed medication.

Yet another configuration would be with respect to the behavioral model, including a portion or all of the trans-theoretical or Stage Process Model and all of its preferred embodiments, as to its location within the hardware and software architecture. In other words, the model could be located for administrative purposes in the server, the platform Server or both. Alternatively, a portion of the model 100 could be downloaded or located in the client personal computer 16, video-set top box, hand-held personal communicator or screen-phone. The model 100 would be flexible in its software architecture in order to allow tuning to adapt to new or specific issues or changes, or enhancements to the model 100 or the client 50's behavior.

Another preferred embodiment shall be the formulation and publication of individually customized information in the form of reports, or graphs, indicating performance and response profiles, educational monographs and tutorials and other materials necessary for providing motivation and education. By storing in the client data base 12 a group of pre-recorded informational data of a generalized nature and accumulating personal response profiles in said client data base 12, it is possible to mix or formulate an individual printed educational document.

The specific content of said document would be adapted to each individual client 50 based upon his education, gender, age, demographic profile, psychological profile and prior response profiles, said educational document and text would be further formulated according to the individual's present behavioral stage 100. The client program 14 would respond to the individual response profiles, individual psychological, demographic and other historical data, and selectively draw upon generalized educational and motivational data in accordance with a behavioral algorithm containing various processes 114 for appropriate and timely insights and guidance for each individual all in accordance with the predetermined model 100. The client program 14 would thus respond to stored information signals indicative of customized recipient information for selecting certain generalized informational and educational prompts and cues of said pre-recorded signals indicative of certain segments to be retrieved selectively and in a given sequence for compilation purposes all in accordance with the predetermined model 100.

All of the aforesaid would be available as text and printed or transmitted by telephone, cable, the mail or delivered in person or by video. In addition, the aforesaid customized text and graphic communications could be accessed by the client 50 via facsimile (FAX) transmission. A further variation on this embodiment would be to transmit the text via modem and telephone or cable by giving each client 50 a telephone number. The system would ask what information he wanted and request his fax number along with a menu of additional options. By giving his current FAX number through touch tone or voice recognition and selecting menu options by the same, the client 50 would be able to receive a customized hard copy of his requested educational and motivational text immediately. Alternatively, the above could be sent via modem to the client's printer.

In instances where the client did not receive a hard copy of FAX but instead received transmission of test and data via wireless, phone or cable, a group of generalized motion picture or taped vignettes could be included for illustrating various situations or incidents of an educational nature. Said transmissions would thereby be available for recording and retention by the client.

Another preferred embodiment would be the utilization of asynchronous transfer mode (ATM) or similar protocols such as ISDN for the transmission of behavioral guidance, since all prior claims and embodiments have relied upon telecommunications which is transmitted or delivered synchronously. As an alternative, this embodiment relates to the asynchronous transmission of information by both wired and wireless means in private and public networks. ATM is equally suited for both data and real time transmissions, such as voice and video. It equally is adaptable to both local and wide-area networks.

There has been described and illustrated herein an improved system and apparatus for interactively changing a behavioral pattern of a client 50. The aforesaid system uniquely extends the prior art of modifying individual behavior to the place where behavior occurs in a customized, personal manner utilizing various computer driven telecommunications platforms. While particular embodiments of the system and apparatus have been described, it is not intended that the invention be limited exactly thereto, as it is intended that the invention be as broad in scope as the art will permit. The foregoing description and drawings will suggest other embodiments and variations within the scope of the claims to those skilled in the art, all of which are intended to be included in the spirit of the invention as herein set forth.

APPENDIX A

*Precontemplation*

Item:

1. As far as I'm concerned, I don't have any problems that need changing.
5. I'm not the problem one. It doesn't make sense for me to be here.
11. Being here is pretty much of a waste of time for me because the problem doesn't have to do with me.
13. I guess I have faults, but there's nothing that I really need to change.
23. I may be part of the problem, but I don't really think I am.
26. All this talk about psychology is boring. Why can't people just forget about their problems?
29. I have worries but so does the next person. Why spend time thinking about them?
31. I would rather cope with my faults than try to change them.

*Contemplation*

Item:

2. I think I might be ready for some self-improvement.
4. It might be worthwhile to work on my problem.
8. I've been thinking that I might want to change something about myself.
12. I'm hoping this place will help me to better understand myself.
15. I have a problem and I really think I should work on it.
19. I wish I had more ideas on how to solve my problem.
21. Maybe this place will be able to help me.
24. I hope that someone here will have some good advice for me.

*Action*

Item:

3. I am doing something about the problems that had been bothering me.
7. I am finally doing some work on my problems.
10. At times my problem is difficult, but I'm working on it.
14. I am really working hard to change.
17. Even though I'm not always successful in changing, I am at least working on my problem.
20. I have started working on my problems but I would like help.
25. Anyone can talk about changing; I'm actually doing something about it.
30. I am actively working on my problem.

*Maintenance*

Item:

6. It worries me that I might slip back on a problem I have already changed, so I am here to seek help.
9. I have been successful in working on my problem but I'm not sure I can keep up the effort on my own.
16. I'm not following through with what I had already changed as well as I had hoped, and I'm here to prevent a relapse of the problem.
18. I thought once I had resolved the problem I would be free of it, but sometimes I still find myself struggling with it.
22. I may need a boost right now to help me maintain the changes I've already made.
27. I'm here to prevent myself from having a relapse of my problem.
28. It is frustrating, but I feel I might be having a recurrence of a problem I thought I had resolved.
32. After all I had done to try to change my problem, every now and again it comes back to haunt me.

A P P E N D I X   B

EXERCISE PROGRAM

Client:   Mary B.   ID# 6723
          Age 37

Metaphor:   Water (enjoys sailing)

Stage Evaluation:   Contemplation

Goal:   Move to Action Stage

KEY TO PROCESS

| | |
|---|---|
| CR: | Consciousness Raising |
| DR: | Dramatic Relief |
| SRE: | Self-Reevaluation |
| ERE: | Environmental Reevaluation |
| HR: | Helping Relationship |
| SL: | Self-Liberation |
| CC: | Counter-Conditioning |
| SC: | Stimulus Control |
| RM: | Reinforcement Management |
| SO.L: | Social Liberation |

DAY ONE

Phone

1:0:0 (Good morning; Good afternoon; Good evening), (Name). I know you'd like to get started on your exercise program. So, if you're open to learning some important information about exercise please,
(CR)        Press 1 for Yes
            Press 2 for No 1:1:00 If Yes (CR) Wonderful, (Name). As you know, researchers have accumulated an impressive body of evidence which shows that a lack of exercise can contribute to physical degeneration, while regular exercise can prevent or delay it. In a review and over 100 studies, Dr. Walter Bortz of Stanford University Medical School, an authority in the field, concluded that most of degenerative changes associated with aging are instead caused by a lack of exercise. You don't have to experience a slow decline of your physical resources; regular, balanced exercise will prevent or lessen the effect of growing older. If you'd like to learn what a balanced exercise program is please, Press 1 for Yes
        Press 2 for No 1:1:1 If Yes: That's good, (Name). Balanced exercise means a program that involves aerobic training for cardiovascular endurance, weight training for strength, and stretching for flexibility.

1:1:2 If No: That's all right. I'd like to call you later this evening to review some important information. Please press 1 if I can call before 8 PM or press 2 if I may call after 8 PM. Thank you, (Name), speak to you soon.

1:2:0 If No:

I understand, (Name). I would like, however, to review with you how exercise can keep you from aging, and will call you later. If I can speak to you before 8 PM, press 1. If I can call you after 8 PM, press 2. Thank you, (Name), speak to you soon.

PAGER
1:3:0 FOR EVERY ONE HOUR SPENT EXERCISING, TWO TO THREE HOURS OF LIFE ARE GAINED, ACCORDING TO THE JOURNAL OF THE AMERICAN
(CR) MEDICAL ASSOCIATION. IF YOU WOULD LIKE TO INCREASE YOUR LIFESPAN, PLEASE PRESS 1 FOR YES.

DAY TWO

Phone

2:0:0  (Good morning; Good afternoon; Good evening), (Name). Before we begin I'd like to ask you a true or false question. A balanced exercise program includes three elements: cardiovascular training, strength training, and flexibility training.
Press 1 for True
Press 2 for False 2:1:0  If True

(CR)
Excellent, (Name). You may be interested to know that the effect of balanced exercise on health and aging was recognized over two thousand years ago, long before modern science began to study it. The ancient Greek physician, Hippocrates, wrote: "All of the parts of the body which have a function, if used in moderation, in exercise and labors in which each is accustomed, become thereby healthy, well developed, and age more slowly, but if unused and left idle, they become liable to disease, defection on growth, and age quickly." The wisdom of the ages is your ally, (Name); you will feel much better on a day-to-day basis with regular, balanced exercise. Did you know that people get fat as they get older because of lack of exercise? If you thought that gaining weight was a natural consequence of aging, please, Press 1 for Yes
Press 2 for No 2:1:1  If Yes:  It must be a relief to learn that getting older doesn't mean getting fatter. You can, and you will, prevent your weight from creeping upward with the passage of time. You're on your way.
(CR)

2:1:2  If No:  Very good, (Name). Your awareness is a valuable asset to use as you begin to work into your exercise program. Keep learning and stay aware.

2:2:0     If False (CR)
>Balanced exercise means a conditioning program that involves the whole body in its range of endurance, strength and flexibility. Aerobic exercise builds your heart and lungs' endurance: the ability to operate for long periods using oxygen at peak efficiency, in effect, to work longer on less fuel. Strength training does exactly that: maintains and/or increases your muscles' ability to perform the activities that you enjoy. Stretching exercise maintains or increases the flexibility in your joints so your body remains supple. If you now understand the principle of balanced exercise please,
>
>     Press 1 for Yes
>     Press 2 for No 2:2:1     If Yes:    Excellent, (Name). Did you know that over two thousand years ago, the Greek physician, Hippocrates, recognized the importance of balanced exercise on health and aging? He said, "All of the parts of the body which have a function, if used in moderation, in exercise and labors in which each is accustomed, become thereby healthy, well developed, and age more slowly, but if unused and left idle, they become liable to disease, defection on growth, and age quickly."

2:2:2     If No:    That's all right, (Name). I would like to call you later to review this information. If you are open to me calling you <u>before</u> 8 PM, please press 1. If you prefer that I call <u>after</u> 8 PM, please press 2.

PAGER
2:3:0
(CR)
STRENGTH TRAINING FIGHTS DISEASE: MODERATE WEIGHT TRAINING 1. LOWERS BLOOD PRESSURE; 2. SLASHES CHOLESTEROL; 3. KEEPS THE HEART STRONG; 4. BUILDS STRONGER BONES; 5. IMPROVES METABOLISM. IF AVOIDING ILLNESS IS IMPORTANT TO YOU, PLEASE PRESS 1. THANK YOU.

DAY THREE

Phone

3:0:0

(DR)

(Good morning; Good afternoon; Good evening), (Name). Sometimes people are reluctant to begin an exercise program because they are self-conscious about their appearance and will feel embarrassed exercising in front of others. If this is something that concerns you, I'd like you to please,
   Press 1 for Yes
   Press 2 for No 3:1:0   If Yes I understand your fear. Many people are anxious about their appearance, particularly when in a health club. Body image is very important to all of us. There is something you can do to help improve the way you perceive your body. If you're open to learning about it, please press 1 for further information.

If (1) pressed: Are you aware we have an effective program to help you modify your body image?

If Yes, please press 1
If no, please press 2

3:1:1   If Yes:  Good, (Name). Please contact your counselor for details of the Body Image Program.

3:1:2   If No:   (Name), our Body Image Improvement Program is available to you, now. It's effective and will improve the quality of your life as you learn to see your body differently, in a positive light. Please contact your counselor for details.

3:2:0

(DR)
(SRE)

If No:   I'm glad that's not a problem for you, (Name). It will be very helpful if you make a list of all the reasons why you've put off getting started on your exercise program. When you're throough, go over your list and stop at the item that causes you the most discomfort, the one that makes you feel anxious. Think about why it makes you feel so uncomfortable. If you're open to making this personal, private list, please, Press 1 for Yes
Press 2 for No

| | | |
|---|---|---|
| 3:2:1:<br><br>(DR)<br>(SRE) | If Yes: | Good, (Name). When you make your list, don't be embarrassed; no one will see it. And if you're reluctant to list a reason because it seems silly to you, that's okay. Many things that people do or think may seem silly, but they are no less important. Your feelings are special, and must be acknowledged. When an item on your list stirs your emotions, spend some time going over in your mind why you feel the way you do. Assess how you feel and think about yourself and exercising, and remember, all exercise, any exercise is positive, to your health when done regularly, moderately, in a balanced manner. |
| 3:2:2<br><br>(SRE)<br>(SRE-Imagery) | If No: | That's okay, (Name). Let's take a few moments to imagine something together. Close your eyes. Take a few deep breaths. Now, I want you to visualize in your mind, a mist covering a country lake in the early morning, and in this mist are your anxieties. The mist is thick at the water's surface but as it rises, it disperses, becoming thinner and thinner, until you can no longer see the mist at all. Everything is clear now; yoou can see the lake in all its beauty. This is your dawn, and you feel light and energetic. This is your dawn, and you can feel the warmth of a new day as the sun greets the sky. This is your day. And you can do whatever you want. You feel good. The cloud of mist has lifted completely and you feel confident, your waters are crystal clear. In the water is strength and you can feel it. In the water lies endurance, and you can feel your reservoir filling. In the water lies flexibility and you can begin to feel the suppleness of a gentle stretch. Now, slowly lift your left arm up over your head, straight toward the ceiling. Gently reach upwards as if you are trying to touch a star. Grasp the star softly in your hand. The star is gently glowing and feels good. Now, (Name), <u>you</u> are that glowing star, and all that is in that star is within you. Strength, flexibility, endurance. They are inside waiting to come out. Now, I want you to slowly lower your arm, still holding the star, gently but firmly. Put the star in a safe place; a pocket, a drawer. It will always be there for you. Think about yourself and exercise. You can do it. |

```
PAGER
3:3:0    WEIGHT TRAINING IS PROBABLY THE FASTEST WAY TO IMPROVE YOUR
         PHYSICAL APPEARANCE, AND THE PSYCHOLOGICAL BENEFITS FROM THAT
(CR)     ARE IMMEASURABLE.  IF YOU BELIEVE YOU WILL FEEL BETTER ABOUT
         YOURSELF IF YOUR BODY LOOKS BETTER, PLEASE PRESS 1.
```

DAY FOUR

Phone

4:0:0     (Good morning; Good afternoon; Good evening), (Name). Nobody enjoys discussing life-threatening issues, yet cancer of the breast or reproductive organs is a concern for all women. And rightly so. Destructive if caught in time, deadly if not. Did you know that know that two independent studies
(CR)     confirmed that young women who had been athletically active contracted these cancers later in life, if at all, than did inactive women? If you knew this, please,
        Press 1 for Yes
        Press 2 for No 4:1:0     If Yes Wonderful, (Name). Knowing this fact is probably one of your incentives for starting your program. Nobody wants cancer. If you'd like to learn more about exercise and health, please, Press 1 for Yes
        Press 2 for No 4:1:1     If Yes:   Good, (Name). Here's more information you'll find of value. In the Journal of the AMA, Dr. Steven Blaun reviewed the death reports of
(CR)              over 218,000 people and found that deaths from cancer of the kidney, colon, brain and blood were less numerous per capita in those that were physically active.

4:1:2     If No:    That's all right, (Name). I'd like to call you later this evening to follow up. If I can call you before 8 PM, Press 1. If you'd rather I call after 8 PM, Press 2.

4:2:0     If No:   That's okay, (Name), not many people do. But it's true. Exercise will lower your risk for breast and cervical cancer. But there's more. If you'd like to know more about exercise and cancer, please Press 1 for Yes
        Press 2 for No 4:2:1:     If Yes:   (Access 4:1:1).

4:2:2:     If No:    (Access 4:1:2)

PAGER
4:3:0     IF YOU ARE INTERESTED IN AVOIDING HEART DISEASE PLEASE PRESS
          1.

(CR)      THANK YOU.  ACCORDING TO THE A.M.A., PHYSICAL INACTIVITY IS A
          SERIOUS RISK FACTOR FOR HEART DISEASE, EQUAL TO SMOKING IN
          ITS CARDIAC CONSEQUENCES.

DAY FIVE

Phone

5:0:0 (Good morning; Good afternoon; Good evening), (Name). Do you feel ready to begin to plan for starting your exercise program? If you are ready to plan for exercise, please,
- Press 1 for Yes
- Press 2 for No
- Press 3 for Don't Know 5:1:0 If Yes (SRE)
(HR)

Congratulations, (Name). You're making progress. Now, I want you to think about whether you wish to exercise in a health club, or by yourself. Do you have proper clothing and shoes? Have you set aside a time of day for regular exercise? I don't want you to answer yet, just think about these things. Consider your choices, options. Make sure you take your personal factors into consideration, so that you find what's right for you. Make notes if it will help. Try to enlist support from a friend, spouse or lover. Perhaps you can exercise together. If not, encourage them to encourage you in your efforts. If you have someone you can turn to for support, please Press 1 for Yes
Press 2 for No 5:1:1 If Yes: Terrific, (Name). Talk to them. Let them know your feelings; how important this is to you. Let this buddy system serve as a pillar of support to ease your burden.

5:1:2 If No: That's okay, (Name). I'm here for you, and will always be here for you as long as you need me. We'll speak at least once a day, everyday. You can depend on me. We're in this together.

5:2:0 If No: That's okay, (Name). We'll move at the pace that's best for you, and soon you'll be well on your way. In the meantime, here's information that you'll find valuable. In Dr. Walter Bortz's study published by the Journal of the AMA, it was found (CR)

that balanced exercise can prevent or slow down those conditions traditionally associated with aging: loss of strength; loss of bone mass; loss of muscle mass; loss of joint flexibility; loss of cardiovascular fitness; decline of immune functioning, and decline of hormone levels. Exercise affects just about every physical process in the body. I know you are aware of these things in a general way. But do you realize just how much you, (Name), can influence the way you age by exercising? If aging gracefully, with as much physical capability and good health as possible is important to you, please Press 1 for Yes
Press 2 for No 5:2:1:   <u>If Yes</u>:   I'm glad to hear that, (Name). Nobody wants their worst fears about getting old to come true. And they don't have to. You can remain physically vibrant and hearty well into old age. It's all up to you. Together, we can accomplish your goals.

5:2:2    <u>If No</u>:    (ACCESS 2:2:2)

5:3:0    <u>If Don't Know</u>:

That's understandable, (Name). You're making a life change and indecision is part of the process. Fact is, if you don't know whether you're ready to prepare to begin, you probably aren't. (ACCESS 5:2:0)

PAGER
5:4:0    (Client opts 5:1:0)

(P)      RESEARCH PROVES THAT IF YOU LIST EVERY PROBLEM YOU EXPECT TO ENCOUNTER INCLUDING SOLUTIONS BEFORE YOU BEGIN TO EXERCISE, YOUR CHANCE OF SUCCESS IMPROVES DRAMATICALLY. IF YOU ACCEPT THIS TRUTH AND WILL MAKE THIS VERY HELPFUL LIST, PLEASE PRESS 1. THANK YOU.

DAY SIX

Phone

6:0:0 (Good morning; Good afternoon; Good evening), (Name). I'd like to ask you a question now about your plans. If you anticipate joining a health club, please,
Press 1
If you plan on a home exercise program, which might include walking or running, please,
Press 2

6:1:0    If 1

(HR)
(CR)

(SRE)

Okay! Joining a health club is for many people the best option. You make a financial commitment, which is an added incentive to continue once you've begun. You'll have many amenities like a steam or sauna, showers, professional equipment and support. The social setting will work for you, too: the sense of community with others who have the same goal; sharing the experiences on the good days, support for difficult workouts when you don't feel up to it. In fact, the hardest thing about exercising at a health club is not the exercise itself but just moving yourself out of your home or job and getting there! Have you begun to think about how you might overcome this natural tendency to avoid the gym?

If Yes, please Press 1
        If No, please Press 2

6:1:1         If Yes: That's good, (Name). Anticipating possible obstacles and dealing with them is always wise and will serve you well as you enter your action stage of change toward exercising.

6:1:2         If No: That's all right, (Name). But I want you to imagine all the possible reasons why you might not feel like, or otherwise be able to, work out. Not matter how silly. Imagine ways you can get to the health club, no matter what comes up.

6:2:0    If 2: That's fine, (Name). Working out at home can be the best option for many people just like you. You won't be intimidated by strange-looking equipment; you don't have to concern yourself with getting to the gym -- you're already there! Self-consciousness? Minimal -- after all, you're by (CR)         yourself. You don't need to be anxious about your appearance; you're close to home, and can attend to

|         | |
|---|---|
| (SRE) | things that need your attention. And, it's free. And so are you. To walk, to run, to watch an exercise video, to adapt an exercise to a home program. It's easy. In fact, the hardest thing about working out at home is how to avoid the mundane distractions of domesticity. Children, the telephone, the TV, etc., so you can actually get your exercise accomplished. Have you thought about how you'll deal with these distractions so you can reach your goal? |

If Yes, Press 1
                    If No, Press 2

6:2:1           <u>If Yes</u>: (ACCESS 6:1:1)

6:2:2           <u>If No</u>: (ACCESS 6:1:2)

PAGER
6:3:0     (Client opts 6:1:0)

(CR)      FIVE WAYS TO FIND A GOOD HEALTH CLUB:
           1.   TRY IT BEFORE JOINING.
           2.   CHECK INSTRUCTORS' QUALIFICATIONS.
           3.   MAKE SURE THE INSTRUCTORS INSTRUCT.
           4.   CHECK WITH LOCAL BETTER BUSINESS BUREAU.
           5.   READ THE FINE PRINT.
           PLEASE PRESS 1 TO CONFIRM RECEIPT OF MESSAGE. THANK YOU.

DAY SEVEN

Phone

7:0:0 (Good morning; Good afternoon; Good evening), (Name). Yesterday you told me that you plan on joining a health club. That's wonderful. You will succeed. I'd like to ask, if I may, when you plan on actually joining. If you are joining a health club <u>today</u>, please,
Press 1
If you think you'll be joining within the next seven days, please,
Press 2
If you feel it will be more than a week before you join, please,
Press 3

7:1:0 <u>If 1</u>

(SL) All right, (Name)! You're obviously motivated go get started ASAP, and that's really terrific. Be proud of yourself. You must feel a real sense of accomplishment. Making a commitment is very liberating. It clears the mind of competing issues, makes you feel, finally, 'Yes I can, and will.' Joining the health club is your first giant step forward. Congratulations! (Access 7:2:0)

7:2:0 <u>If 2</u>

(SL) (Name), take some time to choose carefully; I want you
(HR) to be comfortable with your decision, so your needs will be met. (Name), you told me that you have someone who will support your effort to get involved in an exercise program. If you'll be working out together, please
Press 1
If they'll be offering emotional and moral support but not working out with you, please
Press 2

7:2:1 <u>If 1:</u>

(HR) That's good news! It's so nice to have someone to help you out, be there for you, and gently push when you're working out together.

7:2:2 <u>If 2:</u>

I'm glad to know you have someone to share your experiences -- good and bad -- while you're engaged in your exercise program. Use your buddy system.

7:2:3    If 3

That's all right, (Name)! It will, however, be of benefit to you if you don't let too much time go by before joining. I would like, if I may, to ask you a question. Are you able to make a commitment to yourself to join a health club? If you are, please
      Press 1 for Yes
      Press 2 for No 7:3:0    If 1:

(RM)
Good! Now, at the tone, I want you to record your personal pledge with a simple statement like, "I pledge to join a health club in 8 days, or on this particular date." Afterward, write a note to yourself to confirm the time or date. Wait for the tone, then speak. Thank you. (TONE)

7:3:1    If 2:

Please contact your counselor for insight on how you can learn to make your personal decisions with less inner turmoil and more comfort so you can reach your goal and feel good about yourself.

(Client has chosen 7:1:0)

PAGER
7:4:0

(SRE)
THE BRAIN BENEFITS FROM EXERCISE. YOU WILL THINK WITH GREATER CLARITY. YOU WILL BE MORE MENTALLY ALERT. THIS WILL BE ONE OF YOUR REWARDS FOR JOINING THE GYM. TO RECEIVE THIS REWARD, PLEASE BEGIN EXERCISING WITHIN THE NEXT TWO DAYS AFTER JOINING. COMMIT TO DOING SO BY PLEASE PRESSING (1) ON YOUR PAGER. THANK YOU AND THANK YOURSELF.

PAGER
7:5:1    YOU HAVE MADE A COMMITMENT TO BEING EXERCISING WITHIN THE NEXT TWO DAYS. PLEASE CONFIRM THIS BY PRESSING (1).

PAGER
7:5:2       IF 1:    THANK YOU FOR YOUR CONFIRMATION.

PAGER
7:5:3       IF NO BUTTON PRESSED:  I HAVE NOT RECEIVED YOU CONFIRMATION. IF YOU ARE RECONSIDERING YOUR COMMITMENT, PLEASE PRESS (2). THANK YOU.

DAY EIGHT   (Client opts 7:5:2/7:2:0/7:2:2)

Phone

8:0:0   (Good morning; Good afternoon; Good evening), (Name). Thank you for your commitment to joining a health club and begin working out within two days afterward. If you'll be joining today, please,
  Press 1 for Yes
  Press 2 for No 8:1:0   If Yes (RM)   Great news, (Name)! You're on your way to a new you, and you deserve to reward yourself. Do something, however brief, that you enjoy, whether it's taking five minutes for coffee or free time, or anything else that will act as a personal hug you give to yourself. Can you think of a little something that you can reward yourself with? If you can, please,
  Press 1 for Yes
  Press 2 for No 8:1:1   If 1

(RM)   That's great to hear. Start doing this on a regular basis: a little prize or reward for doing something you feel proud of. Don't wait for others to recognize what you've done. Let this be between you and your innermost self, an intimate, internal pat on back for a job well done.

8:1:2   If 2

That's okay, (Name). I know there's something you can think of to reward yourself; you just may need a little more time to think of it.

8:2:0   If No:

That's okay, (Name), just checking in with you. In the meantime, I want you to think of simple ways to reward yourself when you _do_ join a health club and begin exercising.

PAGER
8:3:0   (Client opts 8:1:0)

DID YOU JOIN A HEALTH CLUB TODAY?  PLEASE PRESS 1 FOR YES, OR 2 FOR NO.

| | | |
|---|---|---|
| 8:3:1 | IF YES: | THAT'S GREAT (NAME). IF YOU BEGAN YOUR EXERCISE PROGRAM TODAY, PLEASE PRESS 2 FOR YES, OR 2 FOR NO. |
| 8:3:2 | IF YES: | WONDERFUL. GIVE YOURSELF A REWARD. WE'LL TALK FURTHER TOMORROW. |
| 8:3:3 | IF NO: | THAT'S LL RIGHT, (NAME). YOU'LL SOON BEGIN. SPEAK TO YOU LATER. |
| 8:3:4 | IF NO: | (ACCESS 8:3:3) |

DAY NINE   (Client opts 8:3:1/8:3:3)

Phone

9:0:0       (Good morning; Good afternoon; Good evening), (Name). I'd
            like you to take a little time today to make a list for
            yourself, just like the one you did when you first enrolled.
            Please divide a sheet of paper into two columns. In one
            column, please list your pros for remaining physically
            inactive. Pros might be: more time to do other things, less
(Stage      physical work, no messy perspiration, etc. In the other
Assess.     column, please list your cons for remaining inactive. Cons
Test)       might be: decreased lifespan, not enough energy, etc. Be
            honest with yourself. Your list is private, so don't worry
            about embarrassment. When you're through, carefully go over
            your list. Make additions if necessary. This list is very
            important, (Name), so please indicate your willingness to
            make it by pressing 1. Thank you, (Name). I'll call you
            later today to go over it with you, so please have it ready.
            Speak to you later.

Phone
9:1:0       Hello, (Name). If you've completed your list of pros and
            cons for remaining inactive, please,
                Press 1 for Yes
                Press 2 for No 9:1:1       If Yes Good work! Now please have your list in front of you,
                    Press the # key when you do...Fine, now please count up
                    the number of pros on your list and enter that number
                    now...Thank you, (Name). Now please total the number of
                    cons on your list and enter that number now...You listed
                    (ACCESS NUMBER) pros and (ACCESS NUMBER) cons. If this
                    is correct, please press 1.

Do you recall the number of pros and cons from your
                    entry interview list? Write these numbers down. It was
                    (ACCESS NUMBER) pros, and (ACCESS NUMBER) cons.

(If cons greater than pros)

It's clear that you're making progress, (Name). Be
                    proud of yourself. Your list of cons is growing, your
                    reasons for starting to exercise increasing. Your list
                    of pros seems weak in comparison to your list of cons.
                    If your urge to start exercising now feels strong to
                    you, please,
                        Press 1 for Yes
                        Press 2 for No 9:1:2    If 1

(SL)
> That's terrific, (Name). Let that feeling of strength fill you like molten steel into a mold. Feel that inner steel set and harden into firmness. Now, imagine this steel as the inner structure of your mind, like girders within a skyscraper. Girders of power and stability. Now, use this new-found strength. Begin to exercise. You have the power.

9:1:3    If 2

> That's okay, (Name). We'll continue until you reach the point where you can't wait any longer to start exercising.

9:2:1    If No:

> That's all right, (Name). I'll call you later to go over it with you. If I can call _before_ 8 PM, please press 1. If you prefer that I call _after_ 8 PM, please press 2.
>
> (Access 9:1:0 for later call)

DAY NINE      (Client opts 9:1:2)

Evaluation:   Client's list = 1 SD↑ CONS, 20% increase

Conclusion:   Ready to proceed to action stage

DAY TEN

Phone

10:0:0 (Good morning; Good afternoon; Good evening), (Name). Congratulations! Judging by your responses yesterday, you're ready to begin exercising. But you already knew that, didn't
(RM) you? You deserve a reward, so please, do something for yourself today to give a moment of pleasure. If you are beginning to exercise today, please,
Press 1 for Yes
Press 2 for No 10:1:0 If Yes (Name), you can do it. You have the power and determination within you. You've grown a lot since you enrolled, and will continue to do so. You're more ready to change your life than ever, so begin this new chapter oof healthy, constructive living now!

10.2:2 If No

That's okay, (Name), but begin soon so you can take advantage of your progress. (Access 10:1:0)

PAGER
10:3:0 TELL YOUR EXERCISE BUDDY YOU'RE STARTING TO EXERCISE TODAY.
(HR) SHARE ALL YOUR FEELINGS, POSITIVE AND NEGATIVE. GET STRONGER, GET FIT, LIVE LONGER.

PAGER
10:4:0 DON'T GIVE IN TO INERTIA. IF YOU FEEL TOO TIRED TO WORK OUT, FORCE YOURSELF TO GET TO THE GYM. REMEMBER: MODERATE
(CC) EXERCISE ENERGIZES: YOU WILL FEEL BETTER <u>AFTER</u> YOU EXERCISE, MORE ALIVE.

PAGER
10:5:0 DON'T BE INFLUENCED BY NEGATIVE IMPACT. DON'T BE DISTRACTED
(CC) FROM YOUR GOAL. DO ALLOW EXERCISE TO BE YOUR ANSWER WHEN YOU FEEL ANXIOUS OR BLAH. GET ACTIVE.

PAGER
10:6:0 WHEN YOU FEEL "WHO NEEDS THIS?" REMEMBER: YOU DO. LOOK AROUND YOU. PEOPLE WHO EXERCISE ARE ENJOYING LIFE MORE. OUR
(SO.L) SOCIETY REWARDS PEOPLE WHO LOOK BETTER AND FEEL BETTER. YOUR CHANCES OF PROFESSIONAL SUCCESS ARE ENHANCED BY EXERCISE. THE WORLD WILL BEGIN TO OPEN UP TO YOU IN A NEW WAY.

I claim:

1. A personalized automated interactive behavioral motivational intervention system for changing a person's behavior comprising:

(a) polling means for polling the person from a number of pre-determined queries and receiving responses from the person to be incorporated into that person's personalized data base, including pre-selected information about that person;

(b) evaluation means for evaluating the person's responses received from said polling means and comparing those responses to said pre-selected data and classifying the person in accordance with at least one of a plurality of different behavioral stages;

(c) program means for programming the person's behavior based upon the responses provided by said polling means and evaluated by said evaluation means to determine the person's preferred behavior to be achieved; and (d) feedback means for providing stimulus to the person as to the success or failure of his progress based upon the responses provided to said polling means and evaluated by said evaluation means as measured by said program means, wherein the person is queried as to particular actions he has undertaken within a given period of time which can be evaluated based upon certain standards that have been established for desired behavior change of the person which are recorded and measured, whereby the person is subsequently alerted as to his success or failure in progressing toward achieving the desired behavioral stage.

2. The system as specified in claim 1 wherein said polling means for creating said database comprising a compact disc and a compact disc player interfacing with a computer.

3. The system as specified in claim 2 wherein said evaluation means for determining the person's behavioral stage comprising a compact disc and a compact disc player that interfaces with a computer.

4. The system as specified in claim 2 wherein said polling means for creating said personalized database comprising the person responding to a 32 item questionnaire.

5. The system as specified in claim 2 wherein said plurality of different behavioral stages comprises a precontemplation stage; contemplation stage; preparation stage; action stage; maintenance stage; and relapse stage.

6. The system as specified in claim 1 wherein said polling means for receiving the person's responses comprising an electronic weight scale that does not allow the person to view his weight.

7. The system specified in claim 1 wherein said polling means for receiving the person's responses comprising an olfactory unit to provide smells in association with said database.

8. The system specified in claim 1 wherein said polling means for receiving the person's responses comprising a voice stress analyzer.

9. The system specified in claim 1 wherein said feedback means for providing stimulus to the person and said polling means for receiving the person's responses comprising using an interactive television system.

10. The system specified in claim 1 wherein said polling means for receiving the person's responses comprising an EEG measuring and recording device.

11. The system specified in claim 1 wherein said feedback means for providing stimulus to the person and said polling means for receiving the person's responses comprising an interactive video system.

12. The system specified in claim 1 wherein said program means for programming the person's behavior and said evaluation means to determine the person's preferred behavior from said database comprising stored information from an optical disc.

13. The system specified in claim 1 wherein said feedback means for providing stimulus to the person and said polling means for receiving the person's responses comprising a cellular phone system.

14. The system specified in claim 1 wherein said feedback means for providing stimulus to the person and said polling means for receiving the person's responses comprising a dual tone multifrequency set having voice recognition.

15. The system specified in claim 1 wherein said feedback means for providing stimulus to the person and said polling means for receiving the person's responses utilizes a Local Area Network (LAN).

16. The system specified in claim 1 wherein said feedback means for providing stimulus to the person and said polling means for receiving the person's responses comprising text and sound message software.

17. The system specified in claim 1 wherein said feedback means for providing stimulus to the person and said polling means for receiving the person's responses utilizes asynchronized transfer mode (ATM).

18. The system specified in claim 1 wherein said feedback means for providing stimulus to the person and said polling means for receiving the person's responses comprising a software agent program having remote programming.

19. The system specified in claim 1 wherein said feedback means for providing stimulus to the person and said polling means for receiving the person's responses comprising a cellular digital packet data (CDPD) network.

20. The system specified in claim 1 wherein said feedback means for providing stimulus to the person and said polling means for receiving the person's responses comprising an interactive video system.

21. The system specified in claim 1 wherein said feedback means for providing stimulus to the person and said polling means for receiving the person's responses comprising a personal digital assistant.

22. The system specified in claim 1 wherein said feedback means for providing stimulus to the person and said polling means for receiving the person's responses comprising a wireless interactive personal communicator having the shape of a woman's compact.

23. The system specified in claim 1 wherein said feedback means for providing stimulus to the person and said polling means for receiving the person's responses comprising a wireless personal communicator.

24. The system specified in claim 1 wherein said feedback means for providing stimulus to the person and said polling means for receiving the person's responses comprising a wireless interactive personal communicator having the configuration of a wristband containing a two-way communication unit.

25. The system specified in claim 1 wherein said polling means for receiving person's responses comprises a timing device for measuring said individual response latency.

26. The system specified in claim 1 wherein said feedback means for providing stimulus to the person comprises a personalized monograph delivering the person's prior responses.

27. The system specified in claim 1 wherein said feedback means comprises a behavioral contract for delivering to the person a specific content based communication received from an earlier response.

28. A method for changing an individual's behavioral state to another behavioral state comprising:

(a) polling means for polling the person from a number of pre-determined queries and receiving responses from the person to be incorporated into that person's personalized data base, including pre-selected information about that person;

(b) evaluation means for evaluating the person's responses received from said polling means and comparing those responses to the pre-selected data and classifying the person in accordance with at least one of a plurality of different behavioral stages;

(c) program means for programming the person's behavior based upon the responses provided by said polling means and evaluated by said evaluation means to determine the person's preferred behavior to be achieved and delivering to the person a number of pro messages correlating to said behavioral stage from said database for a healthy behavior change according to the formula $$PC \rightarrow A \equiv 1SD \uparrow PROS_H;$$

d) program means for programming the person's behavior based upon the responses provided by said polling means and evaluated by said evaluation means to determine the person's preferred behavior to be achieved and delivering to the person a number of con messages correlating to said behavioral stage from said database for not making a healthy behavior change according to the formula $$PC \rightarrow A \equiv 1SD \uparrow CONS_{UNH};$$

e) program means for programming the person's behavior based upon the responses provided by said polling means and evaluated by said evaluation means to determine the person's preferred behavior to be achieved and delivering to the person a number of con messages correlating to said behavioral stage from said database for not making a healthy behavior change according to the formula $$PC \rightarrow A \equiv 0.5SD \downarrow CONS_H;$$

f) program means for programming the person's behavior based upon the responses provided by said polling means and evaluated by said evaluation means to determine the person's preferred behavior to be achieved and delivering to the person a number of pro messages correlating to said behavioral stage from said database for a healthy behavior change according to the formula $$PC \rightarrow A \equiv 0.5SD \downarrow PROS_{UNH};$$

g) feedback means for providing stimulus to the person as to the success or failure of his progress based upon the responses provided to said polling means and evaluated by said evaluation means as measured by said program means, wherein the person is queried as to particular actions he has undertaken within a given period of time which can be evaluated based upon certain standards that have been established for desired behavior change of the person which are recorded and measured, whereby the person is subsequently alerted as to his success or failure in progressing toward achieving the desired behavioral state.

29. The method as specified in claim 27 wherein said polling means is comprised of an IBM-AT compact computer having an 8386 processor or equivalent including a Dialogic D41 4-line speech card or equivalent.

30. The method as specified in claim 28 wherein said database is recorded on a compact disc (CD) recording that is played back to said computer by means of a CD player.

31. The method as specified in claim 28 wherein said database is recorded on a tape cartridge that is played back to a computer by means of a tape cartridge player.

32. The method as specified in claim 28 wherein said polling means for delivering said pro and con messages comprising prompts and cues recorded on a compatible disc recording that is played back to a computer by means of a CD player.

33. The method as specified in claim 28 wherein said polling means for delivering said pro and con messages comprising prompts and cues recorded on a tape cartridge that is played back to a computer by means of a tape cartridge player.

34. The method as specified in claim 27 wherein said polling means and said evaluation means consist of a private telephone network that operates within the confines of an enclosed area.

35. The method as specified in claim 27 wherein said polling means for receiving the persons's responses comprising a dual tone multifrequency telephone set consisting of a standard telephone set hardwired to said telephone network.

36. The method as specified in claim 27 wherein said polling means for receiving the person's responses comprising a dual tone multifrequency telephone set comprising a transportable/cellular telephone.

37. The method specified in claim 27 wherein said polling means for receiving the person's responses to said pro and con messages comprising prompts and cues utilizing an EEG measuring and recording device, heart rate, blood pressure, blood sugar, and cholesterol measuring devices.

38. The method specified in claim 27 wherein said polling means for receiving the person's responses to said pro and con messages comprising prompts and cues with an interactive video system.

39. The method specified in claim 27 wherein said polling means for delivering to the person's said pro and con messages comprising prompts and cues addressing stored information from an optical disc.

40. The method as specified in claim 27 wherein said polling means for receiving the person's responses to said pro and con messages comprising an electronic weight scale having an enclosure which prevents the person from viewing his weight.

41. The method as specified in claim 27 wherein said polling means for receiving the person's responses to said pro and con messages comprising an olfactory unit providing smells indexed to said data base.

42. The method as specified in claim 27 wherein said polling means for receiving the person's responses to said pro and con messages comprising a voice stress analyzer.

43. The method as specified in claim 27 wherein said polling means for creating said personalized data base said polling means for delivering said pro and con messages and said feedback means for providing stimulus to the person comprising an interactive television system.

44. The method as specified in claim 28 wherein said program means includes tracking the whereabouts of the person and selecting a particular behavioral issue from a plurality-of behavioral issues depending on a given time for a given day and activities of the person and said behavioral stage at which the person is in accordance to said evaluation means of said responses.

45. A personalized automated and interactive behavioral and medical guidance system comprising:
- (a) a polling means for creating a data base of personalized input from a plurality of questions indicative of an individual's particular behavioral issue selected from one of a plurality of behavioral issues;
- (b) evaluation means for determining an individual's temporal behavioral stage from said personalized input in said database created by said polling means selected from one of a plurality of behavioral stages; said plurality of behavioral stages comprising a contemplation stage, preparation stage, action stage, maintenance stage, and relapse stage;
- (c) program means including a transmission means for delivering to said individual specific content based communication based upon said evaluation means and said database and selected from one of a plurality of change processes for changing said selected temporal behavioral stage;
- (d) said program means including tracking the whereabouts of said individual and selecting a particular behavioral issue from said plurality of behavioral issues determined by said evaluation means from said personalized input in said database and a communication means depending on a given time for a given day and activities of said individual and said individual's said behavioral stage; and
- (e) feedback means for receiving an individual's response to said content based communication based upon said evaluation means from said personalized input in said database wherein said response is periodically evaluated to determine said behavioral stage and said change processes for readjusting said content based communication.

46. The system as specified in claim 45 wherein said plurality of process changes comprises (a) consciousness raising; (b); self liberation; (c) social liberation; (d) self re-evaluation; (e) environmental re-evaluation; (f) counter conditioning; (g) stimulus control; (h) reinforcement management; (i) dramatic relief; (j) helping relationships; (k) self efficacy; (l) temptations to relapse; (m) decisional pros; and (n) decisional cons.

47. The system as specified in claim 45 wherein said program means comprising a computer-based information metering system that was an optical disc as a transport and storage media and which uses encrypting means to protect data and payment means to permit usage by an individual on a pay-per-view and pay-per-bit-of-information basis.

48. The system as specified in claim 45 wherein said transmission means and said communication means comprising a video conferencing and text system utilizing a plurality of personal computers.

* * * * *